United States Patent [19]

Tsukada et al.

[11] Patent Number: 5,795,767
[45] Date of Patent: Aug. 18, 1998

[54] EPIMERASE

[75] Inventors: Yoji Tsukada, Kyota; Yasuhiro Ohta, Uji; Isafumi Maru, Kyoto, all of Japan

[73] Assignee: Marukin Shoyu Co., Ltd., Kagawa, Japan

[21] Appl. No.: 553,703

[22] PCT Filed: Mar. 24, 1995

[86] PCT No.: PCT/JP95/00541

§ 371 Date: Nov. 22, 1995

§ 102(e) Date: Nov. 22, 1995

[87] PCT Pub. No.: WO95/26399

PCT Pub. Date: Oct. 5, 1995

[30] Foreign Application Priority Data

Mar. 25, 1994 [JP] Japan ................................ 6-056271
Sep. 9, 1994 [JP] Japan ................................ 6-216333

[51] Int. Cl.$^6$ .................... C07H 21/04; C12N 5/00; C12N 9/90; C12N 15/00

[52] U.S. Cl. .................... 435/233; 435/172.1; 435/320.1; 435/325; 536/23.2; 935/22

[58] Field of Search .................... 435/233, 240.2, 435/320.1, 172.1, 325; 424/94.5; 536/23.2; 935/22

[56] References Cited

U.S. PATENT DOCUMENTS 5,071,750  12/1991  Kragl et al. ................ 435/94

OTHER PUBLICATIONS

The Journal of Biological Chemistry, vol. 265, No. 12, Apr. 1990, Hiroyasu Inoue et al., "Molecular Cloning and Sequence Analysis of a cDNA encoding a porcine Kidney Renin–binding Protein", pp. 6556–6561.

The Journal of Biological Chemistry, vol. 110, No. 4, Oct. 1991, Hiroyasu Inoue et al., "Genetic and Molecular Properties of Human and Rat Renin–Binding Proteins with Reference to the Function of the Leucine Zipper Motif", pp. 493–500.

Datta (Jan. 1975) N–Acetylglucosamine 2–Epimerase from Hog Kidney, Methods in Enzymology 41 (Part B): 407–412.

Kragl (Jun. 1992) Reaction technology for biocatalytic processes exemplified by the continuous enzymic synthesis of N–acetylneuraminic acid, Ber. Forschungszent, Juelich, Juel 2583, 186 pp.

Ngo et al. (Feb. 1994) In The Protein Folding Problem and Tertiary Structure Prediction, Eds. Merz et al., Birkhauser, Bostaon, MA, pp. 433 and 492–495.

Primary Examiner—Robert A. Wax
Assistant Examiner—Einar Stole
Attorney, Agent, or Firm—Knobbe Martens, Olson & Bear, LLP

[57] ABSTRACT

A novel polypeptide, acylglucosamine 2-epimerase as shown in FIG. 1 and derivatives thereof, DNA coding for said enzyme, a recombinant vector containing said enzyme, a transformant integrated thereinto said vector, a method for producing said enzyme and a mrthod for producing N-acetylmannosamine and N-acetylneuraminic acid using renin binding protein.

13 Claims, 4 Drawing Sheets

FIG. 1 (1)

```
5'  ATG GAG AAG GAG CGC GAA ACT CTG CAG GCC TGG AAG GAG CGT GTG GGC CAA GAG
    --- --- --- --- --- --- --- --- --- --- --- --- --- --- --- --- --- ---
    Met Glu Lys Glu Arg Glu Thr Leu Gln Ala Trp Lys Glu Arg Val Gly Gln Glu

CTG GAC CGC GTG ATG GCT TTC TGG CTG GAG CAC TCC CAC GAT CGG GAG CAC GGG
    --- --- --- --- --- --- --- --- --- --- --- --- --- --- --- --- --- ---
    Leu Asp Arg Val Met Ala Phe Trp Leu Glu His Ser His Asp Arg Glu His Gly

GGC TTC TTC ACG TGC CTG GGC CGC GAC GGG CGG GTG TAT GAC GAC CTC AAG TAC
    --- --- --- --- --- --- --- --- --- --- --- --- --- --- --- --- --- ---
    Gly Phe Phe Thr Cys Leu Gly Arg Asp Gly Arg Val Tyr Asp Asp Leu Lys Tyr

GTC TGG CTG CAG GGG AGG CAG GTG TGG ATG TAC TGT CGC CTG TAC CGC AAG CTT
    --- --- --- --- --- --- --- --- --- --- --- --- --- --- --- --- --- ---
    Val Trp Leu Gln Gly Arg Gln Val Trp Met Tyr Cys Arg Leu Tyr Arg Lys Leu

GAG CGC TTC CAC CGC CCT GAG CTT CTG GAT GCG GCT AAA GCA GGG GGC GAA TTT
    --- --- --- --- --- --- --- --- --- --- --- --- --- --- --- --- --- ---
    Glu Arg Phe His Arg Pro Glu Leu Leu Asp Ala Ala Lys Ala Gly Gly Glu Phe

TTG CTG CGC CAT GCC CGA GTG GCA CCT CCT GAA AAG AAG TGT GCC TTT GTG CTG
    --- --- --- --- --- --- --- --- --- --- --- --- --- --- --- --- --- ---
    Leu Leu Arg His Ala Arg Val Ala Pro Pro Glu Lys Lys Cys Ala Phe Val Leu

ACG CGG GAC GGC CGG CCC GTC AAG GTG CAG CGG AGC ATC TTC AGT GAG TGC TTC
    --- --- --- --- --- --- --- --- --- --- --- --- --- --- --- --- --- ---
    Thr Arg Asp Gly Arg Pro Val Lys Val Gln Arg Ser Ile Phe Ser Glu Cys Phe

TAC ACC ATG GCC ATG AAC GAG CTG TGG AGG GTG ACG GCG GAG GCA CGG TAC CAG
    --- --- --- --- --- --- --- --- --- --- --- --- --- --- --- --- --- ---
    Tyr Thr Met Ala Met Asn Glu Leu Trp Arg Val Thr Ala Glu Ala Arg Tyr Gln

AGC GAA GCG GTG GAC ATG ATG GAT CAG ATC GTG CAC TGG GTG CGA GAG GAC CCC
    --- --- --- --- --- --- --- --- --- --- --- --- --- --- --- --- --- ---
    Ser Glu Ala Val Asp Met Met Asp Gln Ile Val His Trp Val Arg Glu Asp Pro

TCT GGG CTG GGC CGG CCC CAG CTC CCC GGG GCC GTG GCC TCG GAG TCC ATG GCA
    --- --- --- --- --- --- --- --- --- --- --- --- --- --- --- --- --- ---
    Ser Gly Leu Gly Arg Pro Gln Leu Pro Gly Ala Val Ala Ser Glu Ser Met Ala

GTG CCC ATG ATG CTG CTG TGC CTG GTG GAG CAG CTC GGG GAG GAG GAC GAG GAG
    --- --- --- --- --- --- --- --- --- --- --- --- --- --- --- --- --- ---
    Val Pro Met Met Leu Leu Cys Leu Val Glu Gln Leu Gly Glu Glu Asp Glu Glu

CTG GCA GGC CGC TAC GCG CAG CTG GGG CAC TGG TGC GCT CGG AGG ATC CTG CAG
    --- --- --- --- --- --- --- --- --- --- --- --- --- --- --- --- --- ---
    Leu Ala Gly Arg Tyr Ala Gln Leu Gly His Trp Cys Ala Arg Arg Ile Leu Gln

CAC GTC CAG AGG GAT GGA CAG GCT GTG CTG GAG AAT GTG TCG GAA GAT GGC GAG
    --- --- --- --- --- --- --- --- --- --- --- --- --- --- --- --- --- ---
    His Val Gln Arg Asp Gly Gln Ala Val Leu Glu Asn Val Ser Glu Asp Gly Glu
```

FIG. 1 (2)

```
GAA CTT TCT GGC TGC CTG GGG AGA CAC CAG AAC CCA GGC CAC GCG CTG GAA GCT
--- --- --- --- --- --- --- --- --- --- --- --- --- --- --- --- --- ---
Glu Leu Ser Gly Cys Leu Gly Arg His Gln Asn Pro Gly His Ala Leu Glu Ala

GGC TGG TTC CTG CTC CGC CAC AGC AGC CGG AGC GGT GAC GCC AAA CTT CGA GCC
--- --- --- --- --- --- --- --- --- --- --- --- --- --- --- --- --- ---
Gly Trp Phe Leu Leu Arg His Ser Ser Arg Ser Gly Asp Ala Lys Leu Arg Ala

CAC GTC ATC GAC ACG TTC CTG CTA CTG CCT TTC CGC TCC GGA TGG GAC GCT GAT
--- --- --- --- --- --- --- --- --- --- --- --- --- --- --- --- --- ---
His Val Ile Asp Thr Phe Leu Leu Leu Pro Phe Arg Ser Gly Trp Asp Ala Asp

CAC GGA GGC CTC TTC TAC TTC CAG GAT GCC GAT GGC CTC TGC CCC ACC CAG CTG
--- --- --- --- --- --- --- --- --- --- --- --- --- --- --- --- --- ---
His Gly Gly Leu Phe Tyr Phe Gln Asp Ala Asp Gly Leu Cys Pro Thr Gln Leu

GAG TGG GCC ATG AAG CTC TGG TGG CCG CAC AGC GAA GCC ATG ATC GCC TTT CTC
--- --- --- --- --- --- --- --- --- --- --- --- --- --- --- --- --- ---
Glu Trp Ala Met Lys Leu Trp Trp Pro His Ser Glu Ala Met Ile Ala Phe Leu

ATG GGC TAC AGT GAG AGC GGG GAC CCT GCC TTA CTG CGT CTC TTC TAC CAG GTG
--- --- --- --- --- --- --- --- --- --- --- --- --- --- --- --- --- ---
Met Gly Tyr Ser Glu Ser Gly Asp Pro Ala Leu Leu Arg Leu Phe Tyr Gln Val

GCC GAG TAC ACG TTT CGC CAG TTT CGT GAT CCC GAG TAC GGG GAA TGG TTT GGC
--- --- --- --- --- --- --- --- --- --- --- --- --- --- --- --- --- ---
Ala Glu Tyr Thr Phe Arg Gln Phe Arg Asp Pro Glu Tyr Gly Glu Trp Phe Gly

TAC CTG AAC CGA GAG GGG AAG GTT GCC CTC ACT ATC AAG GGG GGT CCC TTT AAA
--- --- --- --- --- --- --- --- --- --- --- --- --- --- --- --- --- ---
Tyr Leu Asn Arg Glu Gly Lys Val Ala Leu Thr Ile Lys Gly Gly Pro Phe Lys

GGC TGC TTC CAC GTG CCG CGG TGC CTT GCC ATG TGC GAA GAG ATG CTG AGC GCC
--- --- --- --- --- --- --- --- --- --- --- --- --- --- --- --- --- ---
Gly Cys Phe His Val Pro Arg Cys Leu Ala Met Cys Glu Glu Met Leu Ser Ala

CTG CTG AGC CGC CTC GCC TAG 3'
--- --- --- --- --- --- ---
Leu Leu Ser Arg Leu Ala ***
```

EPIMERASE

FIELD OF THE INVENTION

The invention relates to acylglucosamine 2-epimerase and derivatives thereof, a DNA molecule encoding the enzyme, a recombinant vector integrated thereinto the DNA molecule, a transformant containing the vector and a method for producing the epimerase.

The invention relates to a novel polypeptide, acylglucosamine 2-epimerase and derivatives thereof having renin binding activities, a DNA molecule encoding the enzyme, a recombinant vector integrating thereinto the DNA molecule, a transformant containing the vector, a method for producing the epimerase, an antihypertensive agent containing the enzyme or derivative thereof as an essential component, an epimerization agent and methods for producing N-acetylmannosamine and N-acetylneuraminic acid.

BACKGROUND ART

In recent years, N-acetylneuraminic acid is noted as raw materials of drugs. It is known that said N-acetylneuraminic acid may be enzymatically synthesized from N-acetylmannosamine and pyruvic acid using N-acetylneuraminic acid lyase. However, because of expensiveness and difficulty of large-scale preparation of N-acetylmannosamine, a method for preparing N-acetylneuraminic acid by reacting inexpensive N-acetylglucosamine and pyruvic acid in the presence of N-acetylneuraminic acid lyase is proposed (Udo Kragl et al., Angewandte Chemi-International Edition in English, 30, 827–828 (1991)). This method utilizes that acylglucosamine 2-epimerase epimerizes N-acetyl-glucosamine to N-acetylmannosamine. However, acylglucosamine 2-epimerase employed in this method exists only in a trace amount in animal tissues and techniques of large-scale production thereof has not been developed. Accordingly, above-mentioned method may not be employed practically.

On the other hand, Teshima et al. (Clinical Chemistry, 34, 2291–2294 (1988)) disclose that acylglucosamine 2-epimerase is useful for determination of N-acetylhexosamine.

As shown above, acylglucosamine 2-epimerase is a very important enzyme and establishment of an efficient method for production thereof is earnestly desired.

It is known that acylglucosamine 2-epimerase exists in animal tissues. For example, Asis Datta (Methods in Enzymology, 41, 407–412 (1975)) reported that acylglucosamine 2-epimerase existed in porcine kidney. It also widely exists in kidney, liver, mucosal cell, submandibular gland, intestinal mucosa, colon, salivary gland, etc.

Purification of acylglucosamine 2-epimerase from animal tissues is, however, very difficult, and only crude acylglucosamine 2-epimerase is obtained up to the present. For example, Ghosh et al (Methods in Enzymology, 8, 191–195 (1966)) and Asis Datta (Methods in Enzymology, 41, 407–412 (1975)) tried to isolate and purify acylglucosamine 2-epimerase. However, degree of purity is low according to the report of Ghosh. According to Asis Datta, specific activity thereof is about as low as 6 unit/mg protein.

These reports demonstrate that purification of enzyme from crude extract of porcine kidney cortex prepared by homogenizer followed by a combination of conventional purification means, such as protamine concentration, bentonite treatment, DEAE-cellulose column chromatography, adsorption on calcium phosphate gel, etc. is difficult.

The inventors further conduct gel filtration, hydroxyapatite, hydrophobic gel and like a variety of chromatographies and chromatofocusing in addition to said purification means, which do not lead to recovering said enzyme in a purified form due to dilution of enzymatic activities and loss of enzymatic activities caused by inactivation of the enzyme. A trace amount of existence of the enzyme in kidney is one of reasons for difficulties of purification thereof.

Recently, preparation of heterologous proteins using microorganisms becomes relatively easy with the progress of gene recombination techniques. However, because of necessity of isolation of protein for utilizing said means, materials to specify said enzyme, such as DNA probes and antibodies may not be prepared with respect to acylglucosamine 2-epimerase which is obtained only in a crude form. In that case, a conventional alternative method comprises electrophoresis of a partially purified enzyme on polyacrylamide gel, blotting the enzyme on polyvinylidenedifluoride (PVDF) membrane to analyze amino acid sequence thereof, synthesizing DNA probes based on said amino acid sequence to detect a desired gene. However, with respect to this enzyme, the amino acid sequence may not be determined by said method, because N-terminal of acylglucosamine 2-epimerase is blocked by an unknown residue.

As shown above, any method generally employed as gene recombination techniques may not be applicable to acylglucosamine 2-epimerase. A way of producing this enzyme by gene recombination techniques has been closed.

It is an object of the invention to provide a method for producing acylglucosamine 2-epimerase in large quantities at low cost.

In addition, it is another object of the invention to provide acylglucosamine 2-epimerase.

Further, it is another object of the invention to provide DNA molecules coding for acylglucosamine 2-epimerase.

Furthermore, it is another object of the invention to provide recombinant vectors into which a DNA molecule coding for acylglucosamine 2-epimerase is integrated.

Furthermore, it is another object of the invention to provide transformants, wherein recombinant vectors into which a DNA molecule coding for acylglucosamine 2-epimerase is integrated is introduced.

Furthermore, it is another object of the invention to provide antihypertensive agents.

Furthermore, it is another object of the invention to provide epimerizing agents converting N-acetylglucosamine to N-acetylmannosamine.

Furthermore, it is another object of the invention to provide methods for producing N-acetylmannosamine.

Furthermore, it is another object of the invention to provide methods for producing N-acetylneuraminic acid.

Furthermore, it is another object of the invention to provide novel polypeptides.

BRIEF DESCRIPTION OF THE DRAWINGS

FIG. 1 is a scheme showing a nucleotide sequence and an amino acid sequence of acylglucosamine 2-epimerase (SEQ ID NO:9).

In FIG. 2, ☐ demonstrates pBluescript which is a vector DNA. ■ demonstrates a DNA inserted. AGE demonstrates a region of gene coding for acylglucosamine 2-epimerase. Plac demonstrates lac promoter.

In FIG. 3, GlcNAc demonstrates N-acetylglucosamine modified by PMP; ManNAc demonstrates N-acetylmannosamine modified by PMP.

In FIG. 4, lane 1 corresponds to purified acylglucosamine 2-epimerase derived from porcine kidney. Lane 2 corresponds to extract of *Escherichia coli*. Lane 3 corresponds to extract of *Escherichia coli* transformed by pEPI1. Lane 4 corresponds to extract of *Escherichia coli* transformed by pEP114.

DISCLOSURE OF THE INVENTION

Figure 2:
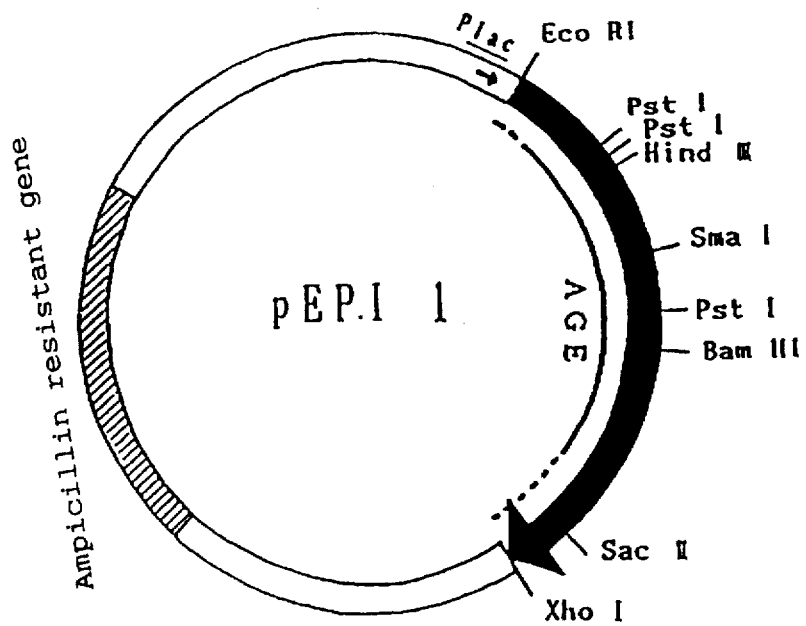
FIG. 2 is a scheme showing a restriction map of plasmid pEPI1.

The inventors conducted extensive research in considering the problems of said prior art, and purified acylglucosamine 2-epimerase in a sufficient degree to allow production of antibody so as to conduct cloning and production of acylglucosamine 2-epimerase using said antibody according to gene engineering techniques. In addition, examination of a variety of biological activities of acylglucosamine 2-epimerase thus obtained becomes clear that acylglucosamine 2-epimerase surprisingly has renin binding activities. The invention has been accomplished based on the findings.

Thus, the invention provides an acylglucosamine 2-epimerase and derivatives thereof, DNA molecules encoding the enzyme, recombinant vectors integrated thereinto the DNA molecule, transformants containing the vector and methods for producing the epimerase, antihypertensive agents containing the enzyme or derivatives thereof as an essential component, epimerizating agents and methods for producing N-acetylmannosamine and N-acetylneuraminic acid according to items 1–22 shown below.

Item 1. A substantially pure acylglucosamine 2-epimerase.

Item 2. An acylglucosamine 2-epimerase or a derivative thereof having said enzymatic activities comprising an amino acid sequence of the following formula (A) (SEQ ID NO:1) or a amino acid sequence of formula (A) a part of which is replaced or deleted (provided that said amino acid sequence, a part of which is replaced or deleted, has acylglucosamine 2-epimerase activities.).

Met Glu Lys Glu Arg Glu Thr Leu Gln Ala Trp Lys

Glu Arg Val Gly Gln Glu Leu Asp Arg Val Met Ala

Phe Trp Leu Glu His Ser His Asp Arg Glu His Gly

-continued
Gly Phe Phe Thr Cys Leu Gly Arg Asp Gly Arg Val

Tyr Asp Asp Leu Lys Tyr Val Trp Leu Gln Gly Arg

Gln Val Trp Met Tyr Cys Arg Leu Tyr Arg Lys Leu

Glu Arg Phe His Arg Pro Glu Leu Leu Asp Ala Ala

Lys Ala Gly Gly Glu Phe Leu Leu Arg His Ala Arg

Val Ala Pro Pro Glu Lys Lys Cys Ala Phe Val Leu

Thr Arg Asp Gly Arg Pro Val Lys Val Gln Arg Ser

Ile Phe Ser Glu Cys Phe Tyr Thr Met Ala Met Asn

Glu Leu Trp Arg Val Thr Ala Glu Ala Arg Tyr Gln

Ser Glu Ala Val Asp Met Met Asp Gln Ile Val His

Trp Val Arg Glu Asp Pro Ser Gly Leu Gly Arg Pro

Gln Leu Pro Gly Ala Val Ala Ser Glu Ser Met Ala

Val Pro Met Met Leu Leu Cys Leu Val Glu Gln Leu

Gly Glu Glu Asp Glu Glu Leu Ala Gly Arg Tyr Ala

Gln Leu Gly His Trp Cys Ala Arg Arg Ile Leu Gln

His Val Gln Arg Asp Gly Gln Ala Val Leu Glu Asn

Val Ser Glu Asp Gly Glu Glu Leu Ser Gly Cys Leu

Gly Arg His Gln Asn Pro Gly His Ala Leu Glu Ala

Gly Trp Phe Leu Leu Arg His Ser Ser Arg Ser Gly

Asp Ala Lys Leu Arg Ala His Val Ile Asp Thr Phe

Leu Leu Leu Pro Phe Arg Ser Gly Trp Asp Ala Asp

His Gly Gly Leu Phe Tyr Phe Gln Asp Ala Asp Gly

Leu Cys Pro Thr Gln Leu Glu Trp Ala Met Lys Leu

Trp Trp Pro His Ser Glu Ala Met Ile Ala Phe Leu

Met Gly Tyr Ser Glu Ser Gly Asp Pro Ala Leu Leu

Arg Leu Phe Tyr Gln Val Ala Glu Tyr Thr Phe Arg

Gln Phe Arg Asp Pro Glu Tyr Gly Glu Trp Phe Gly

Tyr Leu Asn Arg Glu Gly Lys Val Ala Leu Thr Ile

-continued

Lys Gly Gly Pro Phe Lys Gly Cys Phe His Val Pro

Arg Cys Leu Ala Met Cys Glu Glu Met Leu Ser Ala

Leu Leu Ser Arg Leu Ala

Item 3. A DNA molecule coding for acylglucosamine 2-epimerase.

Item 4. A DNA molecule according to item 3 comprising a nucleotide sequence coding for amino acid sequence of the formula (A) (SEQ ID NO:1) or a nucleotide sequence coding for an amino acid sequence of formula (A) a part of which is replaced or deleted (provided that said amino acid sequence, a part of which is replaced or deleted, codes for polypeptide having acylglucosamine 2-epimerase activities.).

Item 5. A DNA molecule according to item 4 comprising a nucleotide sequence of the following formula (X) (SEQ ID NO:5):

ATG GAG AAG GAG CGC GAA ACT CTG CAG GCC TGG AAG (X)
GAG CGT GTG GGC CAA GAG CTG GAC CGC GTG ATG GCT
TTC TGG CTG GAG CAC TCC CAC GAT CGG GAG CAC GGG
GGC TTC TTC ACG TGC CTG GGC CGC GAC GGG CGG GTG
TAT GAC GAC CTC AAG TAC GTC TGG CTG CAG GGG AGG
CAG GTG TGG ATG TAC TGT CGC CTG TAC CGC AAG CTT
GAG CGC TTC CAC CGC CCT GAG CTT CTG GAT GCG GCT
AAA GCA GGG GGC GAA TTT TTG CTG CGC CAT GCC CGA
GTG GCA CCT CCT GAA AAG AAG TGT GCC TTT GTG CTG
ACG CGG GAC GGC CGG CCC GTC AAG GTG CAG CGG AGC
ATC TTC AGT GAG TGC TTC TAC ACC ATG GCC ATG AAC
GAG CTG TGG AGG GTG ACG GCG GAG GCA CGG TAC CAG
AGC GAA GCG GTG GAC ATG ATG GAT CAG ATC GTG CAC
TGG GTG CGA GAG GAC CCC TCT GGG CTG GGC CGG CCC
CAG CTC CCC GGG GCC GTG GCC TCG GAG TCC ATG GCA
GTG CCC ATG ATG CTG CTG TGC CTG GTG GAG CAG CTC
GGG GAG GAG GAC GAG GAG CTG GCA GGC CGC TAC GCG
CAG CTG GGG CAC TGG TGC GCT CGG AGG ATC CTG CAG
CAC GTC CAG AGG GAT GGA CAG GCT GTG CTG GAG AAT
GTG TCG GAA GAT GGC GAG GAA CTT TCT GGC TGC CTG
GGG AGA CAC CAG AAC CCA GGC CAC GCG CTG GAA GCT
GGC TGG TTC CTG CTC CGC CAC AGC AGC CGG AGC GGT
GAC GCC AAA CTT CGA GCC CAC GTC ATC GAC ACG TTC
CTG CTA CTG CCT TTC CGC TCC GGA TGG GAC GCT GAT
CAC GGA GGC CTC TTC TAC TTC CAG GAT GCC GAT GGC
CTC TGC CCC ACC CAG CTG GAG TGG GCC ATG AAG CTC
TGG TGG CCG CAC AGC GAA GCC ATG ATC GCC TTT CTC
ATG GGC TAC AGT GAG AGC GGG GAC CCT GCC TTA CTG
CGT CTC TTC TAC CAG GTG GCC GAG TAC ACG TTT CGC
CAG TTT CGT GAT CCC GAG TAC GGG GAA TGG TTT GGC
TAC CTG AAC CGA GAG GGG AAG GTT GCC CTC ACT ATC
AAG GGG GGT CCC TTT AAA GGC TGC TTC CAC GTG CCG
CGG TGC CTT GCC ATG TGC GAA GAG ATG CTG AGC GCC
CTG CTG AGC CGC CTC GCC TAG

Item 6. A recombinant vector into which a DNA molecule coding for acylglucosamine 2-epimerase is integrated.

Item 7. A recombinant vector according to item 6 comprising a nucleotide sequence coding for the amino acid sequence of the formula (A) (SEQ ID NO:1) or a nucleotide sequence coding for an amino acid sequence of formula (A) a part of which is replaced or deleted (provided that said amino acid sequence, a part of which is replaced or deleted, codes for polypeptide having acylglucosamine 2-epimerase activities.).

Item 8. A recombinant vector according to item 7 comprising a nucleotide sequence coding for the amino acid sequence of the formula (X) (SEQ ID NO:5).

Item 9. A transformant wherein a recombinant vector comprising the DNA molecule of item 3 is introduced into said transformant.

Item 10. A method for producing acylglucosamine 2-epimerase comprising introducing a recombinant vector into which a DNA molecule coding for acylglucosamine 2-epimerase is integrated into a cell to form a transformant, culturing said transformant in medium to produce and accumulate acylglucosamine 2-epimerase in culture, and collecting acylglucosamine 2-epimerase from the culture.

Item 11. An acylglucosamine 2-epimerase having renin binding activities.

Item 12. An epimerase comprising as an essential component a polypeptide as defined in (1) to (3) below:

(1) a polypeptide comprising as an essential sequence said amino acid sequence represented by the formula (A) (SEQ ID NO:1);

(2) a polypeptide represented by the formula (A) in which at least one of positions selected from the group consisting of 10, 13, 21, 23, 27, 33, 45, 47, 51, 71, 72, 76–79, 93, 94, 101, 110, 120, 136, 137, 139, 141, 142, 145, 149, 155, 159, 162, 163, 171, 173, 174, 176, 178, 187, 195, 199–202, 205, 208, 212, 224, 232, 234, 237, 243, 249, 258–261, 263, 266, 267, 269, 270, 272, 275, 282, 287–289, 300, 301, 309, 317, 318, 328, 329, 334, 337, 348, 363, 364, 371, 392, 393, 395, 399, 401 and 402 is replaced or deleted by another amino acid; or (3) a polypeptide formed by adding Pro Ala Pro Ser Pro Ala Pro Thr Pro Ala Cys Arg Gly Ala Glu (SEQ ID NO:6); Pro Ala Pro Leu Gly Ser Leu Pro Ala Val Pro Thr Arg Glu Gly Ser Lys (SEQ ID NO:7); or Lys Gly Asn Lys Ser Trp Gln Asp (SEQ ID NO:8) to N-terminal or C-terminal of polypeptide of formula (A); (provided that said polypeptide, in which a part of formula (A) is replaced or deleted, has acylglucosamine 2-epimerase activities.).

Item 13. A polypeptide of any of (1) to (3) below (provided that polypeptides represented by formulae (R-1), (R-2) and (R-3), listed as SEQ ID NOs:2, 3, and 4, respectively, is excluded.);

(1) a polypeptide comprising as an essential sequence said amino acid sequence represented by the formula (A);

(2) a polypeptide represented by the formula (A) in which at least one of positions selected from the group consisting of 10, 13, 21, 23, 27, 33, 45, 47, 51, 71, 72, 76–79, 93, 94, 101, 110, 120, 136, 137, 139, 141, 142, 145, 149, 155, 159, 162, 163, 171, 173, 174, 176, 178, 187, 195, 199–202, 205, 208, 212, 224, 232, 234, 237, 243, 249, 258–261, 263, 266, 267, 269, 270, 272, 275, 282, 287–289, 300, 301, 309, 317, 318, 328, 329, 334, 337, 348, 363, 364, 371, 392, 393, 395, 399, 401 and 402 is replaced or deleted by another amino acid; or (3) a polypeptide formed by adding Pro Ala Pro Ser Pro Ala Pro Thr Pro Ala Cys Arg Gly Ala Glu (SEQ ID NO:6); Pro Ala Pro Leu Gly Ser Leu Pro Ala Val Pro Thr Arg Glu Gly Ser Lys (SEQ ID NO:7); or Lys Gly Asn Lys Ser Trp Gln Asp (SEQ ID NO:8) to N-terminal or C-terminal of polypeptide of formula (A);

(R-1)

| Met | Glu | Lys | Glu | Arg | Glu | Thr | Leu | Gln | Ala | Trp | Lys |
|---|---|---|---|---|---|---|---|---|---|---|---|
| Glu | Arg | Val | Gly | Gln | Glu | Leu | Asp | Arg | Val | Val | Ala |
| Phe | Trp | Met | Glu | His | Ser | His | Asp | Gln | Glu | His | Gly |
| Gly | Phe | Phe | Thr | Cys | Leu | Gly | Arg | Glu | Gly | Arg | Val |
| Tyr | Asp | Asp | Leu | Lys | Tyr | Val | Trp | Leu | Gln | Gly | Arg |
| Gln | Val | Trp | Met | Tyr | Cys | Arg | Leu | Tyr | Arg | Thr | Phe |
| Glu | Arg | Phe | Arg | His | Ala | Gln | Leu | Leu | Asp | Ala | Ala |
| Lys | Ala | Gly | Gly | Glu | Phe | Leu | Leu | Arg | Tyr | Ala | Arg |
| Val | Ala | Pro | Pro | Gly | Lys | Lys | Cys | Ala | Phe | Val | Leu |
| Thr | Arg | Asp | Gly | Arg | Pro | Val | Lys | Val | Gln | Arg | Thr |
| Ile | Phe | Ser | Glu | Cys | Phe | Tyr | Thr | Met | Ala | Met | Asn |
| Glu | Leu | Trp | Arg | Ala | Thr | Gly | Glu | Val | Arg | Tyr | Gln |
| Thr | Glu | Ala | Val | Glu | Met | Met | Asp | Gln | Ile | Val | His |
| Trp | Val | Gln | Glu | Asp | Ala | Ser | Gly | Leu | Gly | Arg | Pro |
| Gln | Leu | Gln | Gly | Ala | Pro | Ala | Ala | Glu | Pro | Met | Ala |
| Val | Pro | Met | Met | Leu | Leu | Asn | Leu | Val | Glu | Gln | Leu |
| Gly | Glu | Ala | Asp | Glu | Glu | Leu | Ala | Gly | Lys | Tyr | Ala |
| Glu | Leu | Gly | Asp | Trp | Cys | Ala | Arg | Arg | Ile | Leu | Gln |
| His | Val | Gln | Arg | Asp | Gly | Gln | Ala | Val | Leu | Glu | Asn |
| Val | Ser | Glu | Gly | Gly | Lys | Glu | Leu | Pro | Gly | Cys | Leu |
| Gly | Arg | Gln | Gln | Asn | Pro | Gly | His | Thr | Leu | Glu | Ala |
| Gly | Trp | Phe | Leu | Leu | Arg | His | Cys | Ile | Arg | Lys | Gly |
| Asp | Pro | Glu | Leu | Arg | Ala | His | Val | Ile | Asp | Lys | Phe |
| Leu | Leu | Leu | Pro | Phe | His | Ser | Gly | Trp | Asp | Pro | Asp |
| His | Gly | Gly | Leu | Phe | Tyr | Phe | Gln | Asp | Ala | Asp | Asn |
| Phe | Cys | Pro | Thr | Gln | Leu | Glu | Trp | Ala | Met | Lys | Leu |
| Trp | Trp | Pro | His | Ser | Glu | Ala | Met | Ile | Ala | Phe | Leu |
| Met | Gly | Tyr | Ser | Asp | Ser | Gly | Asp | Pro | Val | Leu | Leu |
| Arg | Leu | Phe | Tyr | Gln | Val | Ala | Glu | Tyr | Thr | Phe | Arg |
| Gln | Phe | Arg | Asp | Pro | Glu | Tyr | Gly | Glu | Trp | Phe | Gly |
| Tyr | Leu | Ser | Arg | Glu | Gly | Lys | Val | Ala | Leu | Ser | Ile |
| Lys | Gly | Gly | Pro | Phe | Lys | Gly | Cys | Phe | His | Val | Pro |
| Arg | Cys | Leu | Ala | Met | Cys | Glu | Glu | Met | Leu | Gly | Ala |
| Leu | Leu | Ser | Arg | Pro | Ala | Pro | Ala | Pro | Ser | Pro | Ala |
| Pro | Thr | Pro | Ala | Cys | Arg | Gly | Ala | Glu | | | |

(R-2)

| Met | Glu | Lys | Glu | Arg | Glu | Thr | Leu | Gln | Val | Trp | Lys |
|---|---|---|---|---|---|---|---|---|---|---|---|
| Gln | Arg | Val | Gly | Gln | Glu | Leu | Asp | Ser | Val | Ile | Ala |
| Phe | Trp | Met | Glu | His | Ser | His | Asp | Gln | Glu | His | Gly |
| Gly | Phe | Phe | Thr | Cys | Leu | Gly | Arg | Asp | Gly | Gln | Val |

-continued

| | | | | | | | | | | |
|---|---|---|---|---|---|---|---|---|---|---|
| Tyr | Asp | His | Leu | Lys | Tyr | Val | Trp | Leu | Gln | Gly | Arg |
| Gln | Val | Trp | Met | Tyr | Cys | Arg | Leu | Tyr | Arg | Thr | Phe |
| Glu | Arg | Phe | Arg | Arg | Val | Glu | Leu | Leu | Asp | Ala | Ala |
| Lys | Ala | Gly | Gly | Glu | Phe | Leu | Leu | Ser | Tyr | Ala | Arg |
| Val | Ala | Pro | Pro | Gly | Lys | Lys | Cys | Ala | Phe | Val | Leu |
| Thr | Gln | Asp | Gly | Arg | Pro | Val | Lys | Val | Gln | Arg | Thr |
| Ile | Phe | Ser | Glu | Cys | Phe | Tyr | Thr | Met | Ala | Met | Asn |
| Glu | Leu | Trp | Lys | Val | Thr | Gly | Glu | Met | His | Tyr | Gln |
| Arg | Glu | Ala | Val | Glu | Met | Met | Asp | Gln | Ile | Ile | His |
| Trp | Val | Arg | Glu | Asp | Pro | Ala | Gly | Leu | Gly | Arg | Pro |
| Gln | Leu | Ser | Gly | Thr | Leu | Ala | Thr | Glu | Pro | Met | Ala |
| Val | Pro | Met | Met | Leu | Leu | Asn | Leu | Val | Glu | Gln | Leu |
| Gly | Glu | Glu | Asp | Glu | Glu | Met | Thr | Asp | Lys | Tyr | Ala |
| Glu | Leu | Gly | Asp | Trp | Cys | Ala | His | Arg | Ile | Leu | Gln |
| His | Val | Gln | Arg | Asp | Gly | Gln | Val | Val | Leu | Glu | Asn |
| Val | Ser | Glu | Asp | Gly | Lys | Glu | Leu | Pro | Gly | Cys | Leu |
| Gly | Arg | His | Gln | Asn | Pro | Gly | His | Thr | Leu | Glu | Ala |
| Gly | Trp | Phe | Leu | Leu | Gln | Tyr | Ala | Leu | Arg | Lys | Gly |
| Asp | Pro | Lys | Leu | Gln | Arg | His | Ile | Ile | Asp | Lys | Phe |
| Leu | Leu | Leu | Pro | Phe | His | Ser | Gly | Trp | Asp | Pro | Glu |
| His | Gly | Gly | Leu | Phe | Tyr | Phe | Gln | Asp | Ala | Asp | Asp |
| Leu | Cys | Pro | Thr | Gln | Leu | Glu | Trp | Asn | Met | Lys | Leu |
| Trp | Trp | Pro | His | Thr | Glu | Ala | Met | Ile | Ala | Phe | Leu |
| Met | Gly | Tyr | Arg | Asp | Ser | Gly | Asp | Pro | Ala | Leu | Leu |
| Asn | Leu | Phe | Tyr | Gln | Val | Ala | Glu | Tyr | Thr | Phe | His |
| Gln | Phe | Arg | Asp | Pro | Glu | Tyr | Gly | Glu | Trp | Phe | Gly |
| Tyr | Leu | Asn | Gln | Glu | Gly | Lys | Val | Ala | Leu | Thr | Ile |
| Lys | Gly | Gly | Pro | Phe | Lys | Gly | Cys | Phe | His | Val | Pro |
| Arg | Cys | Leu | Ala | Met | Cys | Glu | Gln | Ile | Leu | Gly | Ala |
| Leu | Leu | Gln | Arg | Leu | Gly | Pro | Ala | Pro | Leu | Gly | Ser |
| Leu | Pro | Ala | Val | Pro | Thr | Arg | Glu | Gly | Ser | Lys | |

(R-3)

| | | | | | | | | | | |
|---|---|---|---|---|---|---|---|---|---|---|
| Met | Glu | Lys | Glu | Arg | Glu | Thr | Leu | Gln | Ala | Trp | Lys |
| Glu | Arg | Val | Gly | Gln | Glu | Leu | Asp | Arg | Val | Met | Ala |
| Phe | Trp | Leu | Glu | His | Ser | His | Asp | Arg | Glu | His | Gly |
| Gly | Phe | Phe | Thr | Cys | Leu | Gly | Arg | Asp | Gly | Arg | Val |
| Tyr | Asp | Asp | Leu | Lys | Tyr | Val | Trp | Leu | Gln | Gly | Arg |
| Gln | Val | Trp | Met | Tyr | Cys | Arg | Leu | Tyr | Arg | Lys | Leu |
| Glu | Arg | Phe | His | Arg | Pro | Glu | Leu | Leu | Asp | Ala | Ala |
| Lys | Ala | Gly | Gly | Glu | Phe | Leu | Leu | Arg | His | Ala | Arg |
| Val | Ala | Pro | Pro | Glu | Lys | Lys | Cys | Ala | Phe | Val | Leu |
| Thr | Arg | Asp | Gly | Arg | Pro | Val | Lys | Val | Gln | Arg | Ser |
| Ile | Phe | Ser | Glu | Cys | Phe | Tyr | Thr | Met | Ala | Met | Asn |
| Glu | Leu | Trp | Arg | Val | Thr | Ala | Glu | Ala | Arg | Tyr | Gln |
| Ser | Glu | Ala | Val | Glu | Met | Met | Asp | Gln | Ile | Val | His |
| Trp | Val | Arg | Glu | Asp | Pro | Ser | Gly | Leu | Gly | Arg | Pro |
| Gln | Leu | Pro | Gly | Ala | Val | Ala | Ser | Glu | Ser | Met | Ala |
| Val | Pro | Met | Met | Leu | Leu | Cys | Leu | Val | Glu | Gln | Leu |
| Gly | Glu | Glu | Asp | Glu | Glu | Leu | Ala | Gly | Arg | Tyr | Ala |
| Gln | Leu | Gly | His | Trp | Cys | Ala | Arg | Arg | Ile | Leu | Gln |
| His | Val | Gln | Arg | Asp | Gly | Gln | Ala | Val | Leu | Glu | Asn |
| Val | Ser | Glu | Asp | Gly | Glu | Leu | Ser | Gly | Cys | Leu | |
| Gly | Arg | His | Gln | Asn | Pro | Gly | His | Ala | Leu | Glu | Ala |
| Gly | Trp | Phe | Leu | Leu | Arg | His | Ser | Ser | Arg | Ser | Gly |
| Asp | Ala | Lys | Leu | Arg | Ala | His | Val | Ile | Asp | Thr | Phe |
| Leu | Leu | Leu | Pro | Phe | Arg | Ser | Gly | Trp | Asp | Ala | Asp |
| Tyr | Gly | Gly | Leu | Phe | Tyr | Phe | Gln | Asp | Ala | Asp | Gly |
| Leu | Cys | Pro | Thr | Gln | Leu | Glu | Trp | Ala | Met | Lys | Leu |
| Trp | Trp | Pro | His | Arg | Gln | Ala | Met | Ile | Ala | Ile | Leu |
| Met | Gly | Tyr | Ser | Glu | Ser | Gly | Asp | Pro | Ala | Leu | Leu |
| Arg | Leu | Phe | Tyr | Gln | Val | Ala | Glu | Tyr | Thr | Phe | Arg |
| Gln | Phe | Arg | Asp | Pro | Glu | Tyr | Gly | Glu | Trp | Phe | Gly |
| Tyr | Leu | Asn | Arg | Glu | Gly | Lys | Val | Ala | Leu | Thr | Ile |
| Lys | Gly | Gly | Pro | Phe | Lys | Gly | Cys | Phe | His | Val | Pro |
| Arg | Cys | Leu | Ala | Met | Cys | Glu | Glu | Met | Leu | Ser | Ala |
| Leu | Leu | Ser | Arg | Leu | Ala | | | | | | |

Item 14. A DNA molecule coding for polypeptide according to item 13.

Item 15. A DNA molecule according to item 14 comprising the nucleotide sequence of formula (X) (SEQ ID NO:5).

Item 16. A recombinant vector into which a DNA molecule coding for acylglucosamine 2-epimerase according to item 14 or 15 is integrated.

Item 17. A transformant wherein a recombinant vector according to item 16 is introduced into said transformant.

Item 18. A method for producing acylglucosamine 2-epimerase having renin binding activities comprising introducing a recombinant vector into which a DNA molecule coding for acylglucosamine 2-epimerase having renin binding activities is integrated into a cell to form a transformant, culturing said transformant in medium to produce and accumulate acylglucosamine 2-epimerase in culture, and collecting acylglucosamine 2-epimerase from the culture.

Item 19. An antihypertensive agent comprising as an essential component acylglucosamine 2-epimerase or a derivative thereof according to item 11 or 12.

Item 20. An epimerizing agent converting N-acetylglucosamine to N-acetylmannosamine comprising as an essential component a polypeptide having renin binding activities.

Item 21. A method for producing N-acetylmannosamine comprising acting a polypeptide having renin binding activities on N-acetylglucosamine.

Item 22. A method for producing N-acetyneuraminic acid comprising acting a polypeptide having renin binding activities and N-acetyneuraminic acid lyase on N-acetylglucosamine and pyruvic acid.

It is known that said proteins (R-1), (R-2) and (R-3), listed as SEQ ID NOs:2, 3, and 4, respectively, have renin binding activities (H. Inoue et al. J. Biochem., 110, p.493–500 (1991)). However, it is not known that said proteins have acylglucosamine 2-epimerase activities. Thus, "protein having renin binding activities" employed in a method for producing N-acetylmannosamine and a method for producing N-acetylneuraminic acid of the invention includes said proteins (R-1), (R-2) and (R-3).

The invention provides a method for producing N-acetylmannosamine characterized in that at least one of said proteins (R-1), (R-2) and (R-3) is applied to.

Further, the invention provides a method for producing N-acetyneuraminic acid characterized in that at least one of said proteins (R-1), (R-2) and (R-3) and N-N-acetyneuraminic acid lyase acts on N-acetylglucosamine and pyruvic acid.

"Protein having renin binding activities", an essential component of epimerizing agent of the invention, comprises said proteins (R-1), (R-2) and (R-3).

Therefore, the invention provides an epimerizing agent converting N-acetylglucosamine to N-acetylmannosamine comprising as an essential component at least one selected from the group consisting of said proteins (R-1), (R-2) and (R-3).

The novel polypeptides of the invention are useful as acylglucosamine 2-epimerase.

Since said items 1–10 are enough as long as they have acylglucosamine 2-epimerase activities, irrespective of existence of renin binding activities, items 1–10 are hereinafter referred to as "first invention".

In addition, said items 11–22 relates to proteins having both acylglucosamine 2-epimerase activities and renin binding activities, and hereinafter referred to as "second invention".

Further, "the invention" includes first invention and second invention.

At least some of acylglucosamine 2-epimerases of the invention have acylglucosamine 2-epimerase activities and renin binding activities. Said epimerases include all proteins having acylglucosamine 2-epimerase activities, irrespective of renin binding activities thereof.

According to the invention, cells transformed by recombinant vector into which DNA molecule coding for acylglucosamine 2-epimerase is integrated are not specifically limited. Example of such cells are *Escherichia coli, Bacillus subtilis, Pseudomonas aeruginosa*, Actinomycetes, Lactic acid bacteria and like bacteria, fungi, yeast and like eucaryotic microorganisms, mouse cells, rat fibroblast, plant cells and like cells as long as cells allow stable retainment and function of plasmids.

For carring out the invention, skilled artisan may suitably select a method for introducing a plasmid into which a DNA molecule coding for acylglucosamine 2-epimerase is integrated into said cell, according to the type of cells. For example, introduction of plasmid into *E. coli* may be carried out according to a method of Hanahan (DNA Cloning, Vol.1, p.109–136 (1985)).

The invention first isolates acylglucosamine 2-epimerase in a form substantially free of impurities and discloses a method for production thereof. The invention first discloses that at least a part of said epimerases have renin binding activities. The second invention includes polypeptides having both acylglucosamine 2-epimerase activities and renin binding activities irrespective of amino acid sequence thereof. For example, the invention includes DNA molecules in which several to one handred and tens of nucleotides at 5' terminal and/or 3' terminal are eliminated by exonuclease, and derivatives of said enzyme encoded by said DNA in which several to tens of amino acids at N-terminal and/or C-terminal are eliminated, as long as said derivatives retain said enzymatic acitivities. Further, the invention includes polypeptides in which at least one amino acid in the amino acid sequence thereof is deleted or replaced by another amino acid according to known point mutation methods, as long as said polypeptides retain said acylglucosamine 2-epimerase activities.

Positions of polypeptides represented by formula (A) allowing replacement and/or deletion are not specifically limited to, but include 10, 13, 21, 23, 27, 33, 45, 47, 51, 71, 72, 76–79, 93, 94, 101, 110, 120, 136, 137, 139, 141, 142, 145, 149, 155, 159, 162, 163, 171, 173, 174, 176, 178, 187, 195, 199–202, 205, 208, 212, 224, 232, 234, 237, 243, 249, 258–261, 263, 266, 267, 269, 270, 272, 275, 282, 287–289, 300, 301, 309, 317, 318, 328, 329, 334, 337, 348, 363, 364, 371, 392, 393, 395, 399, 401 and 402.

Further, the invention include polypeptides to which several to tens of amino acids at N/terminal and/or C-terminal are added, as long as said polypeptides retain said acylglucosamine 2-epimerase activities.

Donors of nucleic acid molecule coding for acylglucosamine 2-epimerase employed in the invention are not specifically limited to, but include animal tissues having said enzymatic activities, such as porcine and human kidneys, kidney, liver, mucosal cell, submandibular gland, intestinal mucosa, colon, salivary gland, etc. of human or rat. Said nucleic acid molecules are obtained from the animal tissues. The nucleic acid molecules include DNAs and RNAs, preferably RNAS.

RNAs coding for acylglucosamine 2-epimerase may be obtained according to a method of Chomczynski et al (Analytical Biochemistry, 162, 156–159, (1987)). RNAs are also obtained as RNAs with polyadenylate tail (poly A tail) according to a method described in Molecular Cloning Second Edition Vol.1, sections 7.26–7.29. cDNAs coding for acylglucosamine 2-epimerase may be easily obtained by using the RNAs with poly A tail.

Conversion of RNA to cDNA may be carried out, for example, according to Current Protocols in Molecular Biology, Vol.1, 5.5.1–5.5.10 (1990). The conversion may also be carried out by using commercially available cDNA synthesis kit (eg. product of Amersham, Stratagene, etc).

cDNA library may be constructed by inserting cDNA into some vectors, for example, phage vectors and plasmid vectors. Construction of cDNA library may be carried out according to a method described in Molecular Cloning Second Edition Vol.2, sections 8.1–8.86.

Means to select transformant retaining cDNA coding for acylglucosamine 2-epimerase from cDNA library constructed are needed. With respect to said enzyme, purified enzyme with required level in the field of recombination of gene was not obtained as stated above. The inventors obtained acylglucosamine 2-epimerase purified enough to produce antibody according to the following method.

First, acylglucosamine 2-epimerase is partially purified according to the method of Asis Datta (Methods in Enzymology, 41, 407–412 (1975)). In the following purification procedure, fractions with high activities and small amount of proteins, i.e., only fractions whose specific activity is higher than specific activity of sample before elution of column are collected, because fractions having activities spread in the process of purification. Specifically, it is found that said enzyme is purified by applying said partially purified sample to hydroxyapatite column and ion-exchange chromatography in this sequence to collect the eluted fraction with highest enzymatic activities, followed by separation thereof by ion-exchange chromatography repeated two times. The enzyme fraction is further purified by HPLC with reverse-phase column (μBondasphere, product of Millipore) to obtain said purified enzyme protein substantially free of impurities. The reverse-phase HPLC is hardly employed for purification of enzymes, since enzymes are easily inactivated during purification. Acylglucosamine 2-epimerase also loses enzymatic activities thereof by said purification, but maintain elicitation ability to produce antibodies. Therefore, antibodies specifically reacted with said enzyme protein are obtained by immunizing rabbit with acylglucosamine 2-epimerase purified by HPLC.

According to said purification steps, for example, 10.5 mg of said purified enzyme protein is obtained from 5.6 kg of porcine kidney cortex.

The DNA molecule coding for acylglucosamine 2-epimerase of the invention may be isolated from constructed cDNAs. The isolation may be carried out by detecting said enzyme with the antibodies using λgt11, λZAP and like vectors as expression vector. The transformant retaining DNA coding for acylglucosamine 2-epimerase produces acylglucosamine 2-epimerase, when exposed by isopropyl-β-D-thiogalactopyranoside (IPTG). The transformant retaining DNA coding for said enzyme may be selected and obtained by binding this to antibody, to which anti-rabbit antibody is bound, followed by reacting the complex with 5-bromo-4-chloro-3-indolylphosphate solution and nitroblue tetrazolium solution.

When resulting DNA coding for acylglucosamine 2-epimerase is inserted into plasmid DNA, $E.$ $coli$ containing said DNA is cultured in a suitable medium to obtain acylglucosamine 2-epimerase. When λZAP is used as a vector, said DNA may be excised cut as a plasmid into vector by simultaneous infection of obtained phage containing said DNA and f1 helper phage. A novel recombinant plasmid containing DNA, for example, represented by formula (X) having 1.2 kbp, coding for acylglucosamine 2-epimerase may be obtained according to the series of operations.

Cells such as $Escherichia$ $coli$ are transformed by using plasinid inserted therein a DNA fragment thus obtained coding for acylglucosamine 2-epimerase. In order to produce acylglucosamine 2-epimerase from transformed cells, transformed cells are cultured in the following conditions to obtain mass of cells.

Culture conditions are different depending on types of cells transformed, and are easily determined in accordance with types of cells. For example, $E.$ $coli$ may be cultured by conventional solid culture method, but is preferably cultured by liquid culture method. In addition, taking $E.$ $coli$ as an example, media employed for culture contain carbon sources, nitrogen sources, inorganic compounds and other nutrient components. Any one of synthetic medium, semisynthetic medium, natural medium and like medium generally employed for culturing bacteria may be used. Examples of carbon sources for said media are glucose, fructose, invert sugar, starch, saccharified starch, sorbitol, glycerol, and like carbohydrate solution, pyruvic acid, malic acid, succinic acid, and like organic acids. Examples of nitrogen sources are ammonium sulfate, ammonium chloride, ammonium nitrate, ammonium phosphate, ammonium hydroxide, ammonium tartrate, ammonium acetate, urea, etc. Substances employed as both carbon and nitrogen sources include peptone, yeast extract, meat extract, corn steep liquor, etc. Examples of inorganic compounds are potassium dihydrogenphosphate, dipotassium hydrogenphosphate, sodium dihydrogenphosphate, disodium hydrogenphosphate, magnesium phosphate, magnesium chloride, potassium chloride, sodium chloride, ferrous sulfate, ferric sulfate, ferric chloride, manganese sulfate, manganese chloride, etc.

Culture time and culture temperature of transformed cells are not specifically limited. Taking $Escherichia$ $coli$ as an example of said cells, culture is conducted at generally 20°–42° C., preferably 30°–37° C., for generally 4–48 hours, preferably 8–14 hours. Under these conditions, conventional shake culture or aeration agitation culture is carried out.

When DNA coding for acylglucosamine 2-epimerase of the invention is bound to a suitable vector to transform a suitable host cell, oxygen concentration of inside or outside of transformed host cell is increased leading to efficient production of said enzyme.

The vector employed in the invention comprises the following elements. Specifically, the vector comprises promoter placed in a correct orientation and position to express DNA coding for acylglucosamine 2-epimerase of the invention and translation activating sequence. Any vector comprising these elements may be employed, but preferably are vectors comprising suitable selected marker and multicopy vectors, which include pBluescript, pUC18, pUC19, pKK223-3 and pTrc99A, etc. When these vectors are employed, intracellular concentration of acylglucosamine 2-epimerase may be elevated by adding about 0.01 mM–100 mM, preferably about 0.1 mM–10 mM of isopropyl-β-D-thiogalactopyranoside to culture medium. Further, pPL-lambda, heat-induced expression vector, may be employed. When employing this vector, intracellular concentration of acylglucosamine 2-epimerase may be increased by elevating temperature of culture medium to 40°–45° C.

Further, increase of productivity and efficiency of said enzyme may be accomplished by deleting terminal DNA of said DNA coding for acylglucosamine 2-epimerase to increase intracellular concentration of acylglucosamine 2-epimerase. For example, production efficiency of acylglucosamine 2-epimerase may be further increased by degradation of said DNA molecule at 5' and/or 3' terminal with exonuclease, etc., while maintaining acylglucosamine 2-epimerase activities.

In addition, productivity of said enzyme may be increased by site-specific mutation or random mutation to replace or delete said DNA at an internal region. For example, site-specific mutation may be introduced by integrating said DNA molecule into pBluescript, M13 and like vectors capable of becoming single strand to prepare single strand DNA containing said DNA molecule; annealing oligonucleotides containing sequence to be mutated or deleted to said single strand DNA; and conducting primer elongation reaction utilizing said oligonucleotides as a primer in the presence of deoxyribonucleotide triphosphate, ATP, Klenow fragment and T4 ligase.

Acylglucosamine 2-epimerase may be extracted from cultured cells. Extraction may be carried out according to conventional enzyme extraction methods. For example, said enzyme may be collected from supernatant by crushing cells with ultrasonic treatment, a variety of mechanical treatments, enzymatic treatments and like methods, followed by separating insoluble matter by centrifugation. The collected crude enzyme may be purified by suitably combining conventional enzyme purification methods. For example, a great amount of purified acylglucosamine 2-epimerase may be obtained by nucleic acid removal treatment, ammonium sulfate treatment, diatomaceous earth treatment, ion-exchange chromatography, etc.

The $Escherichia$ $coli$ strain containing pEPI1 of FIG. 2 integrated thereinto the DNA molecule of FIG. 1 is deposited in National Institute of Bioscience and Human-Technology Agency of Industrial Science and Technology and accession number: FERM BP-4602 is given.

The inventors conducted extensive research on biological activities of polypeptide of formula (A) derived from porcine kidney obtained in second invention and make clear that said enzyme has not only acylglucosamine 2-epimerase activities but also renin binding activities. "Renin binding activities" mean that said polypeptide binds to renin resulting in inhibition of renin activities. The polypeptide of formula (A) is obtained according to the method for producing acylglucosamine 2-epimerase of the invention. In contrast, renin binding protein from porcine kidney of formula (R-3) is obtained according to a method disclosed by Inoue et al (H. Inoue et al., J. Biochem., 110, p.493–500, (1991)). The two proteins (A) and (R-3) obtaining by different purification method are very similar proteins except that they have different amino acids at positions 149, 289, 317 and 318. As shown in the following examples, the polypeptide (A) obtained according to the invention and epimerase from rat kidney have renin binding activities, which indicates that, with respect to at least part of proteins, acylglucosamine 2-epimerase activities and renin binding activities are inseparable. Accordingly, known renin binding proteins (R-1), (R-2) and (R-3) will have epimerase activities. When renin binding proteins have acylglucosamine 2-epimerase activities, said renin binding proteins may be employed as epimerizing agents catalizing the conversion reaction from N-acetylglucosamine to N-acetylmannosamine.

The protein of formula (A) is different from known proteins (R-1), (R-2) and (R-3) in any one of positions 10, 13, 21, 23, 27, 33, 45, 47, 51, 71, 72, 76–79, 93, 94, 101, 110, 120, 136, 137, 139, 141, 142, 145, 149, 155, 159, 162, 163, 171, 173, 174, 176, 178, 187, 195, 199–202, 205, 208, 212, 224, 232, 234, 237, 243, 249, 258–261, 263, 266, 267, 269, 270, 272, 275, 282, 287–289, 300, 301, 309, 317, 318, 328, 329, 334, 337, 348, 363, 364, 371, 392, 393, 395, 399, 401 and 402. However, these proteins have acylglucosamine 2-epimerase activities and renin binding activities so that these positions are not essential for biological activities and may be replaced or deleted. Further, addition of tens of amino acids to the proteins at N-terminal, C-terminal does not affect expression of activities of the proteins. The inventors, in fact, obtained an epimerase obtained by adding amino acids, Lys Gly Asn Lys Ser Trp Gln Asp, to the polypeptide of formula (A) at N-terminal. It is confirmed that said epimerase has sufficient enzymatic activities.

The invention discloses a method for collecting acylglucosamine 2-epimerase produced intracellularly in large amounts comprising separating a DNA molecule coding for acylglucosamine 2-epimerase from animal tissues, preparing a recombinant plasmid containing said DNA molecule, introducing said plasmid into E. coli and like host cell to transform the cell and culturing the transformant.

Renin produces angiotensin I by hydrolyzing angiotensinogen. Angiotensin I is further converted to angiotensin II with angiotensin converting enzyme to express strong hypertensive action by directly constricting smooth muscle of peripheral blood vessel. Angiotensin II also acts on adrenal gland zona glomerulosa to accelerate secretion of aldosterone. As shown above, renin-angiotensin system plays an important role on regulation of blood pressure. Therefore, inhibitors of renin-angiotensin system are developed and widely employed as anti-hypertensive agent. Since acylglucosamine 2-epimerase of the invention binds to renin leading to inhibit activities thereof, acylglucosamine 2-epimerase is useful as an anti-hypertensive agent.

Renin binding proteins have acylglucosamine 2-epimerase activities. Accordingly, renin binding proteins may be employed as epimerizing agent converting N-acetylglucosamine to N-acetylmannosamine. When renin binding proteins act on N-acetylglucosamine, N-acetylmannosamine is obtained. Further, when renin binding proteins and N-acetylneuraminic acid lyase act on N-acetylglucosamine and pyruvic acid, N-acetylneuraminic acid may be obtained by converting N-acetylglucosamine to N-acetylmannosamine with the action of renin binding protein, followed by binding N-acetylmannosamine to pyruvic acid.

According to the invention, the outstanding effects as shown below are exerted.

(1) Highly purified acylglucosamine 2-epimerase may be obtained in large amounts with low costs.

(2) Because microorganisms are employed as starting materials, the method of the invention is not limited with respect to supply of raw material unlike conventional method using animal tissues as raw material. Therefore, production thereof may be carried out at a desired place in required amounts in any time.

(3) Because of high productivity of acylglucosamine 2-epimerase, said enzyme may easily be isolated.

(4) Because high-purity acylglucosamine 2-epimerase may be obtained with low costs, N-acetylneuraminic acid and N-acetylmannosamine may be produced with low costs.

(5) Because high-purity acylglucosamine 2-epimerase may be obtained, it may be employed as assay of N-acetylneuraminic acid and N-acetylhexosamine.

(6) Antihypertensive agents are obtained by using proteins having renin binding activities of the invention.

(7) Because proteins having renin binding activities also have acylglucosamine 2-epimerase activities, said proteins may be employed as epimerizing agents converting N-acetylglucosamine to N-acetylmannosamine.

(8) N-acetylneuraminic acid may be efficiently obtained by reacting proteins of the invention with renin binding activities and N-acetylneuraminic acid lyase with N-acetylglucosamine and pyruvic acid optionally under alkaline conditions.

EXAMPLES

The invention will be described below in greater detail using examples, but the invention is in no way limited to the examples.

Example 1

Production of acylglucosamine 2-epimerase from porcine kidney (1) Purification of acylglucosamine 2-epimerase from porcine kidney Freshly obtained porcine kidney cortex (5.6 kg) supplemented with 12 liter of 3 mM phosphate buffer (pH 7.6) was homogenized with homogenizer. After obtaining supernatant (11 liter) by sequential centrifugation (10,000 rpm, 200 ml/min), cooled distilled water equal volume to the supernatant was added thereto. The resulting mixture was sufficiently stirred and then sequentially centrifuged (10,000 rpm, 200 ml/min) to obtain kidney extract as supernatant. The kidney extract was treated by protamine concentration, bentonite treatment, DEAE-cellulose column chromatography and calcium phosphate gel according to Asis Datta (Methods in Enzymology, 41, 407–412 (1975)) for purification of acylglucosamine 2-epimerase to obtain 387 mg of partially purified enzyme.

Figure 5:
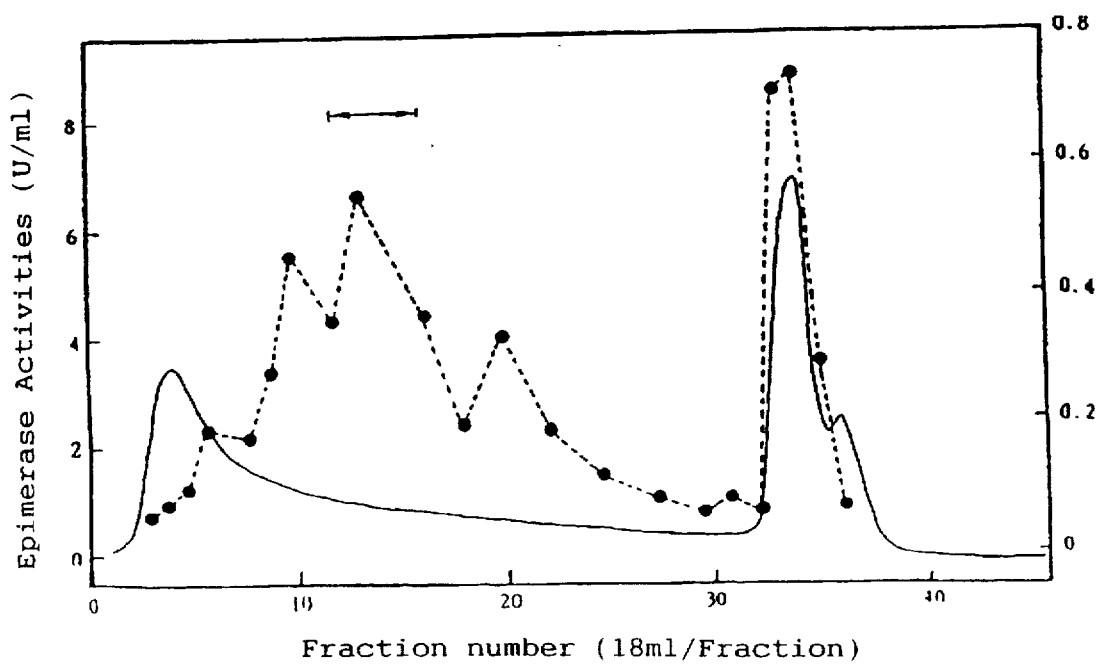
FIG. 5 shows elution pattern of the partially purified enzyme after passing through a hydroxyapatite column. Solid line demonstrates elution of protein determined by ultraviolet absorption (280 nm); Broken line demonstrates activities of acylglucosamine 2-epimerase. Collected fractions are shown by arrows.

Said partially purified enzyme was applied to hydroxyapatite column (inner diameter 26 mm×length 95 mm;

WAKO PURE CHEMICAL CO., LTD.) equilibrated with 10 mM phosphate buffer (pH 7.6) and eluted with the same buffer. Fractions with said enzymatic activities were eluted in widely spread condition according to the treatments of the invention (see, FIG. 5). The 12th to 17th fractions (18 ml×6=108 ml) having said enzymatic activities were treated with salting out techniques using ammonium sulfate to collect fractions saturated with 0–80% by weight of ammonium sulfate. The fractions were dialyzed against 20 mM phosphate buffer (pH 7.6) to give 75.6 mg of dialyzed enzyme. The enzyme was further purified by ion-exchange chromatography in the following conditions to purify the enzyme.

Q-Sepharose (PHARMACIA), one of ion-exchange resins, was filled in a column (inner diameter 26 mm×length 95 mm). The column was equilibrated by 20 mM phosphate buffer (pH 7.6; 500 ml). Said partially purified enzyme (75.6 mg) was adsorbed on the column and eluted by linear gradient using phosphate buffer (pH 7.6) containing 100 mM to 300 mM of potassium chloride. A main peak corresponding to a protein eluted with a potassium chloride concentration of about 180 mM (198 ml) was collected, and then concentrated and dialyzed. The dialyzed enzyme (23.0 mg) was applied to Mono Q column (PHARMACIA) to adsorb said enzyme on the column. The adsorbed enzyme was eluted by linear gradient using phosphate buffer (pH 7.6) containing 200 mM to 300 mM of potassium chloride. A peak corresponding to a protein eluted with a potassium chloride concentration of about 220 mM was collected, and then desalted by gel filtration column. An activity of the enzyme (15.9 mg) thus obtained was 21 units/mg protein as a specific activity, which is 3.5 time as high as the activity (purity) of the protein (6 units/mg protein) reported by Asis Datta (Methods in Enzymology, 41, 407–412 (1975)).

Further, the resulting enzyme was purified to remove low-molecular-weight materials and trace amount of impurities by HPLC using reverse phase column.

μBondasphere 5 μC4-300 Å (inner diameter 3.9 mm×length 150 mm) (MILLIPORE) was employed as reverse phase column. Said purified enzyme (2 mg) was subjected to the column equilibrated with 0.1% (V/V) TFA aqueous solution. Said purified enzyme retained in the column was eluted by linear gradient using 0.1% (V/V) TFA aqueous solution containing 0 to 80% (V/V) of acetonitrile. A main peak protein determined by ultraviolet absorption (280 nm) was collected and dried in vacuo. Said procedure was repeated 6 times to obtain the enzyme (10.5 mg). The enzyme thus obtained loses biological activities but is substantially free of impurities.

(2) Antibodies specifically bound to acylglucosamine 2-epimerase

Nine weeks old rabbits (JAPANESE WHITE) were immunized with said purified acylglucosamine 2-epimerase (5.2 mg). Blood of said rabbit was gathered partially and wholly to obtain 150 ml of antiserum. IgG was purified from the antiserum using Protein A Sepharose according to the description on page 24 of New Biochemical Experimental Course 12, Ed. Japan Biochemistry Organization, Molecular Immunology III, (1992).

Example 2

Cloning of cDNA coding for acylglucosamine 2-epimerase (1) Production of mRNA from porcine kidney Kidney cortex was cut out from porcine kidney. RNAs (4.9 mg) were obtained from 2 g of kidney cortex according to the method of Chomczynski et al (Analytical Biochemistry, 162, 156, (1987)). RNAs with poly(A) tail (67 μg) were then obtained by adsorbing said RNA on oligo-dT-cellulose column, followed by elution thereof.

(2) Preparation of cDNA library

A cDNA library was prepared from the RNAs with poly(A) tail (5 μg) thus obtained using a ZAP-cDNA synthesis kit (STRATAGENE). The library obtained was 4.5× $10^{12}$ of plaque forming unit.

(3) Screening of gene of acylglucosamine 2-epimerase

Screening of recombinant containing DNA coding for acylglucosamine 2-epimerase was carried out according to immunostaining method using antibody of example 1 and picoBlue Immunoscreening Kit (STRATAGENE).

64 positive phages were obtained by screening 1,200,000 of plaques according to said method. Optionally 12 strains were selected from said positive phages. E. coli was infected by said strains with f1 helper phage so as to integrate cDNAs into plasmids. E. coli strain with plasmid having acylglucosamine 2-epimerase activities was selected. The plasmid was taken out from E. coli selected to prepare a recombinant plasmid pEPI1 (4.3 kbp) containing insertional fragment (1.4 kbp). Restriction map of pEPI1 is shown in FIG. 2.

The E. coli into which pEPI1 (4.3 kbp) was introduced was deposited under accession number FERM BP-4602 in National Institute of Bioscience and Human-Technology Agency of Industrial Science and Technology on Mar. 11, 1994.

(4) Determination of acylglucosamine 2-epimerase activities

In order to determine acylglucosamine 2-epimerase activities in E. coli, E. coli XL1-Blue was inoculated in LB medium (1% peptone, 0.5% yeast extract, 1% NaCl, pH 7.0) containing 100 mg/liter of ampicillin and then shake-cultured. Further, for efficient production of said enzyme, isopropyl-β-D-thiogalactopyranoside was added to the medium within a final concentration of 1 mM when starting culture. The resulting medium was cultured at 37° C. for 12 hours and then centrifuged (5,000 rpm, 10 minutes) to obtain pellet of cells. Cell extract was obtained by ultrasonic disruption of cells. The cell extract was reacted at 37° C. for 30 minutes at a final volume of 0.5 ml in the presence of 40 mM of N-acetylmannosamine (NACALAI TESQUE) or 40 mM of N-acetylglucosamine (NACALAI TESQUE), 4 mM of adenosine-triphosphate (KOJIN Co., Ltd.), 10 mM of magnesium chloride and 100 mM of Tris-HCl buffer (pH 7.5). The resulting reaction mixture was boiled for 3 minutes in boiled water to stop the reaction. The enzymatic activities were determined by assaying N-acetyl-mannosamine or N-acetylglucosamine of reaction supernatant prepared by centrifugation (12,000 rpm, 5 minutes) of said reaction mixture. In the determination, it is difficult to determine N-acetylmannosamine and N-acetylglucosamine as they are by HPLC. In order to convert these compounds to 1-phenyl-3-methyl-5-pyrazolone (PMP) derivatives according to the method of Honda et al (Analytical Biochemistry, 180, 351–357 (1989)), 10 μl of said reaction supernatant was removed to 1.5 ml volume of microtube, to which 50 μl of 0.5M PMP methanol solution and 50 μl of 0.3M NaOH aqueous solution was added, subsequently the mixture was reacted at 70° C. for 30 minutes. The reaction mixture was cooled at room temperature for 10 minutes, and then neutralized with 150 μl of 0.1M hydrochloric acid aqueous solution. To the neutralized solution was added 200 μl of chloroform, and the mixture was mixed to separate unreacted PMP in chloroform layer to obtain PMP-N-acetylhexosamine in aqueous layer. After removing chloroform layer, the aqueous layer was dried in vacuo. The dried residue was dissolved in 250 μl of distilled water, 10 μl of which was injected to HPLC for separation and determination. HPLC analysis was carried out using LC-6A system (SHIMADZU CORP.) and column (Cosmosil 5C18-AR (inner diameter 6.0 mm×length 150 mm), NACALAI TESQUE) with a mixture of acetonitrile and 50 mM phosphate buffer (pH 7.0) (2:8) as mobile phase at a rate of 1 ml/min. Detection were performed by absorption amount of ultraviolet at 245 nm. The enzymatic activities are shown as unit. One unit is defined as activity to produce 1 μmol of N-acetylglucosamine per 1 minute from the reaction of N-acetylmannosamine as substrate.

Figure 3:
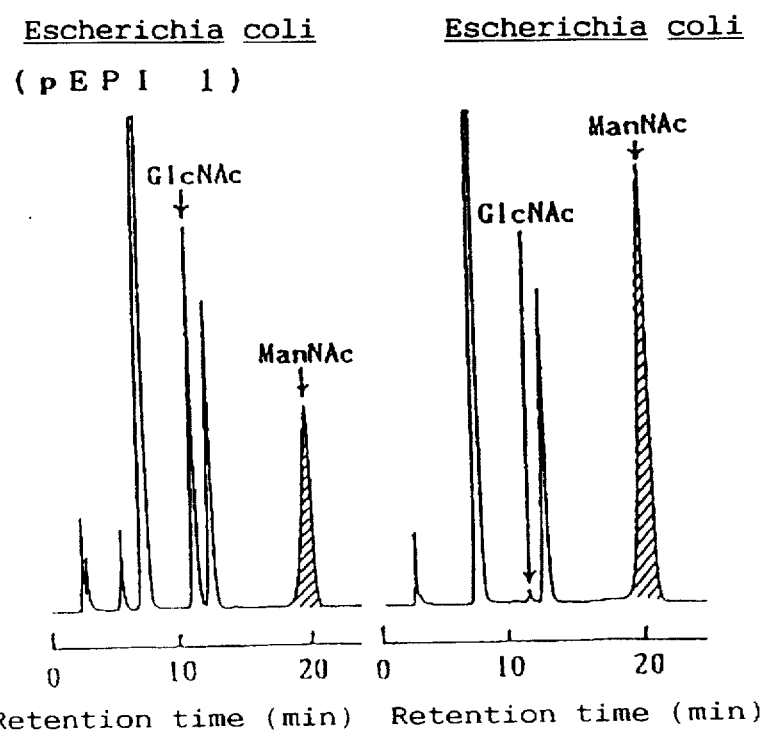
FIG. 3 is a chromatogram analyzed by HPLC of a reaction mixture modified by PMP. The reaction mixture was prepared by reacting extracts either from cells transformed by recombinant plasmids or cells without transformation in a reaction medium containing N-acetylmannosamine as a substrate.
Figure 4:
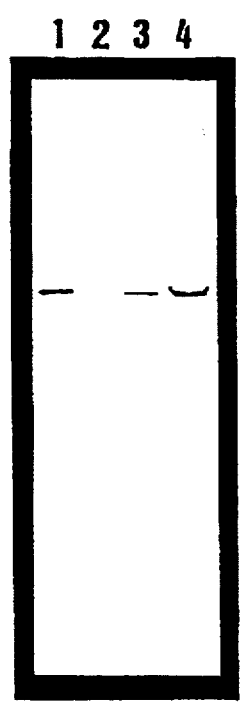
FIG. 4 is a diagram showing immunological staining after SDS-electrophoresis and western blotting of purified acylglucosamine 2-epimerase derived from porcine kidney and cell extracts of E. coli.

Consequently, when N-acetylmannosamine was contained in the reaction mixture, N-acetylmannosamine was converted to N-acetylglucosamine in the presence of cell extract (see FIG. 3). Similarly, N-acetylglucosamine was converted to N-acetylmannosamine in the presence of cell extract. In each reaction, N-acetylglucosamine : N-acetylmannosamine reached a equilibrium condition of 75 : 25. No conversion was observed without addition of said cell extract to said mixture. Furthermore, antibodies directed to purified acylglucosamine 2-epimerase was reacted with a band of 45,000 daltons in western blotting. The test results, as a whole, demonstrate that cloned gene produce protein corresponding to acylglucosamine 2-epimerase. Further, acylglucosamine 2-epimerase activities of the cell extract correspond to 10 unit production per 1 liter of culture medium, showing that specific activities of cell extract was 0.03 U/mg, which is similar to extract of porcine kidney cortex. The results demonstrate that acylglucosamine 2-epimerase, conventionally obtained only from aminal tissues, may be produced by microorganisms transformed by plasmid pEPI1.

(5) Determination of nucleotide sequence of acylglucosamine 2-epimerase

A necleotide sequence of 1.4 kbp of DNA fragment was determined by dideoxy method whose basic principle was a process described by Sanger et al (Proceedings of The National Academy of Sciences of the United States of America, 74, 5463–5467 (1977)). Because a vector employed in pEPI1 was pBluescript capable of becoming single strand, deletion mutant of the vector was prepared, and then nucleotide sequence thereof was determined. The nucleotide sequence coding for acylglucosamine 2-epimerase-is shown in FIG. 1 (SEQ ID NO:9). Further, amino acid sequence of polypeptide obtained by translation of said nucleotide sequence coding for the enzyme is shown simultaneously.

Example 3
Production of acylglucosamine 2-epimerase by microorganisms (1) Construction of plasmid producing acylglucosamine 2-epimerase with high efficiency Highly efficient production of acylglucosamine 2-epimerase by microorganisms become possible by construction of deletion plasmid of pEPI1. The plasmid pEPI1 (20 μg) in 500 μl solution was cut at 37° C. for 4 hours with restriction enzymes of 100 units of SacI and 100 units of XbaI. The mixture treated by restriction enzymes was treated at 75° C. for 15 minutes, extracted by phenol/chloroform (1:1) and then precipitated with ethanol. The precipitate was dissolved in sterilized water at a concentration of 1 μg/μl. Tens of deletion plasmids were prepared from the solution using ExoIII/Mung Deletion Kit (STRATAGENE), in which pEP114 produced acylglucosamine 2-epimerase with high efficiency. E. coli XL1-Blue transformed by plasmid pEP114 was cultured in LB medium containing 100 μl/ml of ampicillin and 1 mM of isopropyl-β-D-thiogalactopyranoside at 37° C. for 12 hours. Cell extract was prepared from cells of said culture. Acylglucosamine 2-epimerase activities of cell extract correspond to about 1,000 units per 1 liter of culture medium, and specific activities thereof was 1.6 U/mg, which was 53 times as much as extract of porcine kidney cortex.

(2) Production of acylglucosamine 2-epimerase

The plasmid pEP114 provides useful means for producing a larger amount of acylglucosamine 2-epimerase in E. coli. Culture of E. coli to obtain acylglucosamine 2-epimerase is much easier than preparation thereof from animal tissue.

Culture thereof was carried out by inoculating E. coli XL1-Blue transformed by plasmid pEP114 in two shaking flasks (2-liter volume) containing 500 ml of LB medium (1% peptone, 0.5% yeast extract, 1% NaCl, pH 7.0) containing 100 mg/liter of ampicillin and 1 mM IPTG, then shake-cultured the flasks. After culture at 37° C. for 12 hours, cultured materials were collected by centrifugation and washed with saline two times. The cells were then suspended in 50 ml of phosphate buffer (pH 7.6) containing 1mM of EDTA and 0.05% of 2-mercaptethanol, and then disrupted by ultrasonic oscillation (UR-200P, TOMY SEIKO CO.). Precipitate was removed by centrifugation to obtain cell extract. To the cell extract was added protamine sulfate at a concentration of 0.03%(W/V). Centrifugation was conducted as nucleic acid removal treatment. The supernatant was subjected to salting out treatment with ammonium sulfate. Fractions saturated with 20–80% ammonium sulfate were collected and dialyzed against phosphate buffer. The dialyzed solution was applied to DEAE-cellulose (WHATMAN) column (diameter 50mm×length 100 mm) equilibrated with said phosphate buffer for adsorption thereof. Elution of adsorbed proteins was carried out by adding suitable concentration of potassium chloride to said phosphate buffer. Acylglucosamine 2-epimerase activities were existed in fractions with potassium chloride concentration of 75–100 mM, which were collected, concentrated, desalted and then applied to Q-Sepharose (PHARMACIA) (inner diameter 1 cm×length 5 cm). Elution of adsorbed proteins was carried out by linear gradient using said phosphate buffer containing 100 mM of potassium chloride and said phosphate buffer containing 300 mM of potassium chloride. Fractions with acylglucosamine 2-epimerase activities were collected, concentrated by said membrane filter and desalted to obtain about 700 unit (33 mg) of purified cloned acylglucosamine 2-epimerase.

Example 4
Purification of acylglucosamine 2-epimerase from rat kidney

Acylglucosamine 2-epimerase from rat kidney was purified in the same manner as Example 1(1) using 300 g of rat kidney to give 0.15 mg of acylglucosamine 2-epimerase, provided that acylglucosamine 2-epimerase was purified using Mono Q column in place of reverse phase column (pBondasphere 5 μC4-300 Å) which causes inactivation of enzyme.

Example 5
Inhibition of renin activities by acylglucosamine 2-epimerase (1)

A 2.5 mU of commercially available renin (SIGMA) and 0.25 pmol of cloned acylglucosamine 2-epimerase obtained in example 3 were added to 40 μl of buffer A (0.1M sodium phosphate buffer (pH 6.5), 1 mM EDTA, 1 μM leupeptin, 0.05% bovine serum albumin). The mixture was reacted at 37° C. for 1 hour. After the reaction, 960 μl of chilled buffer A was added thereto to adjust the total volume thereof to 1 ml. To 250 μl of buffer A were added a part of said diluted solution thus prepared (25 μl) and 0.4 mg/ml of angiotensinogen (SIGMA) and phenylmethylsulfonyl fluoride at a final concentration of 2.5 mM. The reaction mixture was then reacted at 37° C. for 30 minutes. The solution was treated for 3 minutes in boiled water to stop the reaction. After centrifugation (14,000 rpm, 10 minutes), angiotensin I released in supernatant was determined. The results were shown in Table 1.

TABLE 1

| Cloned epimerase (pmol) | Remaining renin activities (%) |
|---|---|
| 0 | 100 |
| 1 | 87 |
| 3 | 66 |
| 10 | 54 |
| 25 | 48 |

Example 6

Inhibition of renin activities by acylglucosamine 2-epimerase (1)

Renin inhibition activities of acylgiucosamine 2-epimerase were determined in the same manner as example 5 except that rat acylglucosamine 2-epimerase obtained in example 4 was employed in place of cloned acylglucosamine 2-epimerase obtained in example 3. The results are shown in Table 2.

TABLE 2

| Rat kidney epimerase (pmol) | Remaining renin activities (%) |
|---|---|
| 0 | 100 |
| 1 | 98 |
| 10 | 88 |
| 50 | 48 |

Example 7

Binding reaction of renin and acylglucosamine 2-epimerase (1)

To 100 μl buffer A was added 25 mU of renin (SIGMA) and 140 pmol of cloned acylglucosamine 2-epimerase obtained in example 3, and the resulting mixture was reacted at 37° C. for 1 hour.

Said reaction solution (100 μl) was fractionated by gel filtration chromatography (Column, Superose 12 HR 10/30; Mobile phase, 50 mM sodium phosphate buffer (pH 7.5) −150 mM sodium chloride; flow rate 1 ml/min; Detection, ultraviolet (280 nm)). Renin activities of each fraction were assayed to determine change of molecular weight of renin.

The renin activities of fractions eluted by said gel filtration chromatography were determined according to the method of example 5. Consequently, in case of no addition of acylglucosamine 2-epimerase, renin activities were eluted at a position of about 40,000 daltons corresponding to molecular weight of renin. However, in case of addition of acylglucosamine 2-epimerase, renin activities were eluted at a position of about 60,000 daltons, demonstrating that said enzyme is attached to renin to increase molecular weight thereof.

The high-molecular-weight renin obtaind in this example coincided very closely with molecular weight (about 60,000 daltons) of high-molecular-weight type (HMW) renin determined by gel filtration chromatography, :i.e., the complex of renin with renin binding protein reported by Takahashi et al (J. Biochem., 93, 1583–1594 (1983)). Therefore, said acylglucosamine 2-epimerase has renin binding activities.

Example 8

Binding reaction of renin and acylglucosamine 2-epimerase (2)

Determination of molecular weight thereof was carried out by gel filtration chromatography in the same manner as example 7 except that rat acylglucosamine 2-epimerase obtained in example 4 was employed in place of cloned acylglucosamine 2-epimerase obtained in example 3. Consequently, molecular weight of renin was increased as high as 60,000 daltons as shown in example 7.

Example 9

A method for producing N-acetvlmannosamine with protein having renin binding activities Production of N-acetylmannosamine was carried out from inexpensive N-acetylglucosamine. A mixture (100 ml) consisting of 10 g of N-acetylglucosamine, 5 mg of protein having renin binding activities obtained in example 3, 4 mM ATP and 10 mM $MgCl_2$ was adjusted at a pH of 7.5, and the mixture was reacted at 37° C. for 24 hours. The reaction solution was concentrated to give syrup in vacuo. To the syrup obtained was added 40 ml of ethanol and the solution was heated in a boiled water bath for 10 minutes and then allowed to stand for 3 hours. Since N-acetylglucosamine is insoluble and N-acetylmannosamine is insoluble, precipitate (N-acetylglucosamine) was filtered off and the filtrate was concentrated to give 2 g of N-acetylmannosamine with a purity of at least 91% in vacuo.

Example 10

Production of sialic acid using protein having renin binding activities

Production of N-acetylneuraminic acid was carried out by acting the protein having renin binding activities and N-acetylneuraminic acid lyase on N-acetylglucosamine and pyruvic acid.

A solution prepared by dissolving 22 g of N-acetylglucosamine and 11 g of pyruvic acid in 50 mM of Tris-HCl buffer (pH 7.5) containing 5 mM ATP and 5 mM $MgCl_2$. To the solution was added 15 mg of protein having renin binding activities obtained in example 3 and 500 unit of N-acetylneuraminic acid lyase, and the total volume of the solution was adjusted to 0.5 liter. The mixture was reacted at 30° C. for 48 hours. After the reaction, 12.4 g of N-acetylneuraminic acid was produced in the reaction mixture. Reaction product was isolated by ion-exchange chromatography with Dowex 11 (DOW CHEMICAL CO.). After concentration, 10.3 g of N-acetylneuraminic acid was obtained by lyophilization.

We claim:

1. An isolated DNA molecule coding for acylglucosamine 2-epimerase isolated from mammalian species.

2. An isolated DNA molecule coding for acylglucosamine 2-epimerase, comprising a nucleotide sequence coding for a polypeptide having the amino acid sequence of SEQ ID NO:1 or a nucleotide sequence coding for a polypeptide having a partial amino acid sequence of SEQ ID NO:1 wherein the polypeptide having said partial amino acid sequence has acylglucosamine 2-epimerase activity.

3. A DNA molecule according to claim 2 comprising the nucleic acid sequence of SEQ ID NO:5.

4. A recombinant vector into which a DNA molecule coding for acylglucosamine 2-epimerase isolated from mammalian species is integrated.

5. A recombinant vector into which a DNA molecule coding for acylglucosamine 2-epimerase is integrated, comprising a nucleotide sequence coding for a polypeptide having the amino acid sequence of SEQ ID NO:1 or a nucleotide sequence coding for a polypeptide having a partial amino acid sequence of SEQ ID NO:1 wherein the polypeptide having said partial amino acid sequence has acylglucosamine 2-epimerase activity.

6. A recombinant vector according to claim 5 comprising the nucleic acid sequence of SEQ ID NO:5.

7. A transformant wherein a recombinant vector comprising the DNA molecule of claim 2 is introduced into said transformant.

8. A method for producing acylglucosamine 2-epimerase comprising introducing a recombinant vector into which a DNA molecule of claim 2 is integrated into a cell to form a transformant, culturing said transformant in medium to produce and accumulated acylglucosamine 2-epimerase in culture, and collecting acylglucosamine 2-epimerase from the culture.

9. A DNA molecule coding for a polypeptide having an amino acid sequence other than the amino acid sequence listed as SEQ ID NO:2, NO:3, or NO:4, said polypeptide comprising an amino acid sequence being selected from the group consisting of:

(1) the amino acid sequence listed as SEQ ID NO:1;

(2) an amino acid sequence of SEQ ID NO:1 from which at least one position selected from the group consisting of 10, 13, 21, 23, 27, 33, 45, 47, 51, 71, 72, 76–79, 93, 94, 101, 110, 120, 136, 137, 139, 141, 142, 145, 149, 155, 162, 163, 171, 173, 174, 176, 178, 187, 195, 199–202, 205, 208 212, 224, 232, 234, 237, 243, 249, 258–261, 263, 266, 267, 269, 270, 272, 275, 282, 287–289, 300, 301, 309, 317, 318, 328, 329, 334, 337, 348, 236, 364, 371, 392, 393, 395, 399, 401, and 402 is eliminated or replaced with another amino acid; and (3) a combination of: (a) a partial amino acid sequence of SEQ ID NO:1 wherein a polypeptide having said partial amino acid sequence has acylglucosamine 2-epimerase activity; and (b) an amino acid sequence selected from the group consisting of SEQ ID NO:6, NO:7, and NO:8, wherein a peptide having sequence (b) is attached to the N-terminal or C-terminal of the polypeptide having sequence (a).

10. A DNA molecule according to claim 9 comprising the nucleotide sequence of SEQ ID NO:5.

11. A recombinant vector into which a DNA molecule coding for acylglucosamine 2-epimerase according to claim 9 or 10 is integrated.

12. A transformant wherein a recombinant vector according to claim 11 is introduced into said transformant.

13. A method for producing acylglucosamine 2-epimerase having renin binding activities comprising introducing a recombinant vector into which a DNA molecule coding for acylglucosamine 2-epimerase having renin binding activities isolated from mammalian species is integrated into a cell to form a transformant, culturing said transformant in medium to produce and accumulated acylglucosamine 2-epimerase in culture, and collecting acylglucosamine 2-epimerase from the culture.

* * * * *

UNITED STATES PATENT AND TRADEMARK OFFICE
CERTIFICATE OF CORRECTION

PATENT NO. : 5,795,767
DATED : August 18, 1998
INVENTOR(S) : Yoji Tsukada, Yasuhiro Ohta and Isafumi Maru It is certified that error appears in the above-identified patent and that said Letters Patent is hereby corrected as shown below:

On the title page: Item [75] Inventors: first line, delete "Kyota" and insert --Kyoto--.

Signed and Sealed this

First Day of December, 1998

*Attest:*

BRUCE LEHMAN

*Attesting Officer*          Commissioner of Patents and Trademarks

UNITED STATES PATENT AND TRADEMARK OFFICE
CERTIFICATE OF CORRECTION

PATENT NO. : 5,795,767
DATED : August 18, 1998
INVENTOR(S) : Yoji Tsukada, Yasuhiro Ohta, and Isafumi Maru It is certified that error appears in the above-identified patent and that said Letters Patent is hereby corrected as shown below:

On the title page: Item [56] References Cited, OTHER PUBLICATION, delete "encoding" and insert --Encoding--.

On the title page: Item [56] References Cited, OTHER PUBLICATION, delete "porcine" and insert --Porcine--.

On the title page: Item [57] ABSTRACT, line 5, delete "mrthod" and insert --method--.

Column 39, line 2, insert --159,-- between 155, and 162,.

Column 39, line 6, delete "236" and insert --363--.

Signed and Sealed this

Thirtieth Day of March, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 402 amino acids
      ( B ) TYPE: amino acid
      ( C ) STRANDEDNESS: single
      ( D ) TOPOLOGY: linear ( i i ) MOLECULE TYPE: peptide ( v ) FRAGMENT TYPE: N-terminal ( x i ) SEQUENCE DESCRIPTION: SEQ ID NO:1:

```
Met Glu Lys Glu Arg Glu Thr Leu Gln Ala Trp Lys Glu Arg Val Gly
  1               5                  10                  15
Gln Glu Leu Asp Arg Val Met Ala Phe Trp Leu Glu His Ser His Asp
             20                  25                  30
Arg Glu His Gly Gly Phe Phe Thr Cys Leu Gly Arg Asp Gly Arg Val
         35                  40                  45
Tyr Asp Asp Leu Lys Tyr Val Trp Leu Gln Gly Arg Gln Val Trp Met
 50                  55                  60
Tyr Cys Arg Leu Tyr Arg Lys Leu Glu Arg Phe His Arg Pro Glu Leu
 65                  70                  75                  80
Leu Asp Ala Ala Lys Ala Gly Gly Glu Phe Leu Leu Arg His Ala Arg
                 85                  90                  95
Val Ala Pro Pro Glu Lys Lys Cys Ala Phe Val Leu Thr Arg Asp Gly
            100                 105                 110
Arg Pro Val Lys Val Gln Arg Ser Ile Phe Ser Glu Cys Phe Tyr Thr
            115                 120                 125
Met Ala Met Asn Glu Leu Trp Arg Val Thr Ala Glu Ala Arg Tyr Gln
        130                 135                 140
Ser Glu Ala Val Asp Met Met Asp Gln Ile Val His Trp Val Arg Glu
145                 150                 155                 160
Asp Pro Ser Gly Leu Gly Arg Pro Gln Leu Pro Gly Ala Val Ala Ser
                165                 170                 175
Glu Ser Met Ala Val Pro Met Met Leu Leu Cys Leu Val Glu Gln Leu
            180                 185                 190
Gly Glu Glu Asp Glu Glu Leu Ala Gly Arg Tyr Ala Gln Leu Gly His
        195                 200                 205
Trp Cys Ala Arg Arg Ile Leu Gln His Val Gln Arg Asp Gly Gln Ala
210                 215                 220
Val Leu Glu Asn Val Ser Glu Asp Gly Glu Glu Leu Ser Gly Cys Leu
225                 230                 235                 240
Gly Arg His Gln Asn Pro Gly His Ala Leu Glu Ala Gly Trp Phe Leu
                245                 250                 255
Leu Arg His Ser Ser Arg Ser Gly Asp Ala Lys Leu Arg Ala His Val
            260                 265                 270
Ile Asp Thr Phe Leu Leu Leu Pro Phe Arg Ser Gly Trp Asp Ala Asp
        275                 280                 285
His Gly Gly Leu Phe Tyr Phe Gln Asp Ala Asp Gly Leu Cys Pro Thr
    290                 295                 300
Gln Leu Glu Trp Ala Met Lys Leu Trp Trp Pro His Ser Glu Ala Met
```

|  | 305 |  |  |  | 310 |  |  |  | 315 |  |  |  | 320 |
|---|---|---|---|---|---|---|---|---|---|---|---|---|---|
| Ile | Ala | Phe | Leu | Met 325 | Gly | Tyr | Ser | Glu 330 | Ser | Gly | Asp | Pro | Ala | Leu 335 | Leu |
| Arg | Leu | Phe | Tyr 340 | Gln | Val | Ala | Glu | Tyr 345 | Thr | Phe | Arg | Gln | Phe 350 | Arg | Asp |
| Pro | Glu | Tyr 355 | Gly | Glu | Trp | Phe | Gly 360 | Tyr | Leu | Asn | Arg | Glu 365 | Gly | Lys | Val |
| Ala | Leu 370 | Thr | Ile | Lys | Gly | Gly 375 | Pro | Phe | Lys | Gly | Cys 380 | Phe | His | Val | Pro |
| Arg 385 | Cys | Leu | Ala | Met | Cys 390 | Glu | Glu | Met | Leu | Ser 395 | Ala | Leu | Leu | Ser | Arg 400 |
| Leu | Ala |

(2) INFORMATION FOR SEQ ID NO:2:

(i) SEQUENCE CHARACTERISTICS:
(A) LENGTH: 417 amino acids
(B) TYPE: amino acid
(C) STRANDEDNESS: single
(D) TOPOLOGY: linear (ii) MOLECULE TYPE: peptide (v) FRAGMENT TYPE: N-terminal (xi) SEQUENCE DESCRIPTION: SEQ ID NO:2:

| Met 1 | Glu | Lys | Glu | Arg 5 | Glu | Thr | Leu | Gln | Ala 10 | Trp | Lys | Glu | Arg | Val 15 | Gly |
|---|---|---|---|---|---|---|---|---|---|---|---|---|---|---|---|
| Gln | Glu | Leu | Asp 20 | Arg | Val | Val | Ala | Phe 25 | Trp | Met | Glu | His | Ser 30 | His | Asp |
| Gln | Glu | His 35 | Gly | Gly | Phe | Phe | Thr 40 | Cys | Leu | Gly | Arg | Glu 45 | Gly | Arg | Val |
| Tyr | Asp 50 | Asp | Leu | Lys | Tyr | Val 55 | Trp | Leu | Gln | Gly | Arg 60 | Gln | Val | Trp | Met |
| Tyr 65 | Cys | Arg | Leu | Tyr | Arg 70 | Thr | Phe | Glu | Arg | Phe 75 | Arg | His | Ala | Gln | Leu 80 |
| Leu | Asp | Ala | Ala | Lys 85 | Ala | Gly | Gly | Glu | Phe 90 | Leu | Leu | Arg | Tyr | Ala 95 | Arg |
| Val | Ala | Pro | Pro 100 | Gly | Lys | Lys | Cys | Ala 105 | Phe | Val | Leu | Thr | Arg 110 | Asp | Gly |
| Arg | Pro | Val 115 | Lys | Val | Gln | Arg | Thr 120 | Ile | Phe | Ser | Glu | Cys 125 | Phe | Tyr | Thr |
| Met | Ala 130 | Met | Asn | Glu | Leu | Trp 135 | Arg | Ala | Thr | Gly | Glu 140 | Val | Arg | Tyr | Gln |
| Thr 145 | Glu | Ala | Val | Glu | Met 150 | Met | Asp | Gln | Ile | Val 155 | His | Trp | Val | Gln | Glu 160 |
| Asp | Ala | Ser | Gly | Leu 165 | Gly | Arg | Pro | Gln | Leu 170 | Gln | Gly | Ala | Pro | Ala 175 | Ala |
| Glu | Pro | Met | Ala 180 | Val | Pro | Met | Met 185 | Leu | Leu | Asn | Leu | Val 190 | Glu | Gln | Leu |
| Gly | Glu | Ala 195 | Asp | Glu | Glu | Leu | Ala 200 | Gly | Lys | Tyr | Ala | Glu 205 | Leu | Gly | Asp |
| Trp | Cys 210 | Ala | Arg | Arg | Ile | Leu 215 | Gln | His | Val | Gln | Arg 220 | Asp | Gly | Gln | Ala |
| Val 225 | Leu | Glu | Asn | Val | Ser 230 | Glu | Gly | Gly | Lys | Glu 235 | Leu | Pro | Gly | Cys | Leu 240 |
| Gly | Arg | Gln | Gln | Asn | Pro | Gly | His | Thr | Leu | Glu | Ala | Gly | Trp | Phe | Leu |

|     |     |     |     | 245 |     |     |     | 250 |     |     |     | 255 |     |     |
|-----|-----|-----|-----|-----|-----|-----|-----|-----|-----|-----|-----|-----|-----|-----|
| Leu | Arg | His | Cys | Ile | Arg | Lys | Gly | Asp | Pro | Glu | Leu | Arg | Ala | His | Val |
|     |     |     | 260 |     |     |     | 265 |     |     |     | 270 |     |     |     |
| Ile | Asp | Lys | Phe | Leu | Leu | Leu | Pro | Phe | His | Ser | Gly | Trp | Asp | Pro | Asp |
|     |     | 275 |     |     |     | 280 |     |     |     | 285 |     |     |     |     |
| His | Gly | Gly | Leu | Phe | Tyr | Phe | Gln | Asp | Ala | Asp | Asn | Phe | Cys | Pro | Thr |
|     | 290 |     |     |     | 295 |     |     |     | 300 |     |     |     |     |     |
| Gln | Leu | Glu | Trp | Ala | Met | Lys | Leu | Trp | Trp | Pro | His | Ser | Glu | Ala | Met |
| 305 |     |     |     | 310 |     |     |     |     | 315 |     |     |     |     | 320 |
| Ile | Ala | Phe | Leu | Met | Gly | Tyr | Ser | Asp | Ser | Gly | Asp | Pro | Val | Leu | Leu |
|     |     |     | 325 |     |     |     | 330 |     |     |     | 335 |     |     |
| Arg | Leu | Phe | Tyr | Gln | Val | Ala | Glu | Tyr | Thr | Phe | Arg | Gln | Phe | Arg | Asp |
|     |     | 340 |     |     |     | 345 |     |     |     | 350 |     |     |     |
| Pro | Glu | Tyr | Gly | Glu | Trp | Phe | Gly | Tyr | Leu | Ser | Arg | Glu | Gly | Lys | Val |
|     |     | 355 |     |     |     | 360 |     |     |     | 365 |     |     |     |
| Ala | Leu | Ser | Ile | Lys | Gly | Gly | Pro | Phe | Lys | Gly | Cys | Phe | His | Val | Pro |
|     | 370 |     |     |     | 375 |     |     |     | 380 |     |     |     |     |
| Arg | Cys | Leu | Ala | Met | Cys | Glu | Glu | Met | Leu | Gly | Ala | Leu | Leu | Ser | Arg |
| 385 |     |     |     | 390 |     |     |     | 395 |     |     |     | 400 |
| Pro | Ala | Pro | Ala | Pro | Ser | Pro | Ala | Pro | Thr | Pro | Ala | Cys | Arg | Gly | Ala |
|     |     |     | 405 |     |     |     | 410 |     |     |     | 415 |     |
| Glu |

(2) INFORMATION FOR SEQ ID NO:3:

(i) SEQUENCE CHARACTERISTICS:
        (A) LENGTH: 419 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:3:

| Met | Glu | Lys | Glu | Arg | Glu | Thr | Leu | Gln | Val | Trp | Lys | Gln | Arg | Val | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |
| Gln | Glu | Leu | Asp | Ser | Val | Ile | Ala | Phe | Trp | Met | Glu | His | Ser | His | Asp |
|     |     |     | 20  |     |     |     |     | 25  |     |     |     |     | 30  |     |
| Gln | Glu | His | Gly | Gly | Phe | Phe | Thr | Cys | Leu | Gly | Arg | Asp | Gly | Gln | Val |
|     |     |     | 35  |     |     |     | 40  |     |     |     |     | 45  |     |
| Tyr | Asp | His | Leu | Lys | Tyr | Val | Trp | Leu | Gln | Gly | Arg | Gln | Val | Trp | Met |
|     | 50  |     |     |     |     | 55  |     |     |     | 60  |     |     |     |
| Tyr | Cys | Arg | Leu | Tyr | Arg | Thr | Phe | Glu | Arg | Phe | Arg | Arg | Val | Glu | Leu |
| 65  |     |     |     |     | 70  |     |     |     |     | 75  |     |     |     |     | 80  |
| Leu | Asp | Ala | Ala | Lys | Ala | Gly | Gly | Glu | Phe | Leu | Leu | Ser | Tyr | Ala | Arg |
|     |     |     |     | 85  |     |     |     |     | 90  |     |     |     |     | 95  |
| Val | Ala | Pro | Pro | Gly | Lys | Lys | Cys | Ala | Phe | Val | Leu | Thr | Gln | Asp | Gly |
|     |     |     | 100 |     |     |     |     | 105 |     |     |     |     | 110 |     |
| Arg | Pro | Val | Lys | Val | Gln | Arg | Thr | Ile | Phe | Ser | Glu | Cys | Phe | Tyr | Thr |
|     |     | 115 |     |     |     |     | 120 |     |     |     |     | 125 |     |
| Met | Ala | Met | Asn | Glu | Leu | Trp | Lys | Val | Thr | Gly | Glu | Met | His | Tyr | Gln |
|     | 130 |     |     |     |     | 135 |     |     |     | 140 |     |     |     |
| Arg | Glu | Ala | Val | Glu | Met | Met | Asp | Gln | Ile | Ile | His | Trp | Val | Arg | Glu |
| 145 |     |     |     |     | 150 |     |     |     |     | 155 |     |     |     |     | 160 |
| Asp | Pro | Ala | Gly | Leu | Gly | Arg | Pro | Gln | Leu | Ser | Gly | Thr | Leu | Ala | Thr |

|     |     |     |     | 165 |     |     |     | 170 |     |     |     | 175 |     |
|---|---|---|---|---|---|---|---|---|---|---|---|---|---|

Glu Pro Met Ala Val Pro Met Met Leu Leu Asn Leu Val Glu Gln Leu
            180             185                 190

Gly Glu Glu Asp Glu Glu Met Thr Asp Lys Tyr Ala Glu Leu Gly Asp
        195             200                 205

Trp Cys Ala His Arg Ile Leu Gln His Val Gln Arg Asp Gly Gln Val
    210                 215                 220

Val Leu Glu Asn Val Ser Glu Asp Gly Lys Glu Leu Pro Gly Cys Leu
225             230                 235                     240

Gly Arg His Gln Asn Pro Gly His Thr Leu Glu Ala Gly Trp Phe Leu
                245             250                 255

Leu Gln Tyr Ala Leu Arg Lys Gly Asp Pro Lys Leu Gln Arg His Ile
            260             265                 270

Ile Asp Lys Phe Leu Leu Leu Pro Phe His Ser Gly Trp Asp Pro Glu
        275             280                 285

His Gly Gly Leu Phe Tyr Phe Gln Asp Ala Asp Asp Leu Cys Pro Thr
    290                 295                 300

Gln Leu Glu Trp Asn Met Lys Leu Trp Trp Pro His Thr Glu Ala Met
305             310                 315                     320

Ile Ala Phe Leu Met Gly Tyr Arg Asp Ser Gly Asp Pro Ala Leu Leu
                325             330                 335

Asn Leu Phe Tyr Gln Val Ala Glu Tyr Thr Phe His Gln Phe Arg Asp
            340             345                 350

Pro Glu Tyr Gly Glu Trp Phe Gly Tyr Leu Asn Gln Glu Gly Lys Val
            355             360                 365

Ala Leu Thr Ile Lys Gly Gly Pro Phe Lys Gly Cys Phe His Val Pro
    370                 375                 380

Arg Cys Leu Ala Met Cys Glu Gln Ile Leu Gly Ala Leu Leu Gln Arg
385             390                 395                     400

Leu Gly Pro Ala Pro Leu Gly Ser Leu Pro Ala Val Pro Thr Arg Glu
            405             410                 415

Gly Ser Lys ( 2 ) INFORMATION FOR SEQ ID NO:4:

( i ) SEQUENCE CHARACTERISTICS:
        ( A ) LENGTH: 402 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:4:

Met Glu Lys Glu Arg Glu Thr Leu Gln Ala Trp Lys Glu Arg Val Gly
1               5                   10                  15

Gln Glu Leu Asp Arg Val Met Ala Phe Trp Leu Glu His Ser His Asp
            20              25                  30

Arg Glu His Gly Gly Phe Phe Thr Cys Leu Gly Arg Asp Gly Arg Val
        35              40                  45

Tyr Asp Asp Leu Lys Tyr Val Trp Leu Gln Gly Arg Gln Val Trp Met
    50              55                  60

Tyr Cys Arg Leu Tyr Arg Lys Leu Glu Arg Phe His Arg Pro Glu Leu
65              70                  75                      80

Leu Asp Ala Ala Lys Ala Gly Gly Glu Phe Leu Leu Arg His Ala Arg

|     |     |     |     | 85  |     |     |     |     | 90  |     |     |     |     | 95  |     |
|-----|-----|-----|-----|-----|-----|-----|-----|-----|-----|-----|-----|-----|-----|-----|-----|
| Val | Ala | Pro | Pro | Glu | Lys | Lys | Cys | Ala | Phe | Val | Leu | Thr | Arg | Asp | Gly |
|     |     |     | 100 |     |     |     |     | 105 |     |     |     | 110 |     |     |     |
| Arg | Pro | Val | Lys | Val | Gln | Arg | Ser | Ile | Phe | Ser | Glu | Cys | Phe | Tyr | Thr |
|     |     | 115 |     |     |     | 120 |     |     |     |     | 125 |     |     |     |     |
| Met | Ala | Met | Asn | Glu | Leu | Trp | Arg | Val | Thr | Ala | Glu | Ala | Arg | Tyr | Gln |
|     | 130 |     |     |     |     | 135 |     |     |     | 140 |     |     |     |     |     |
| Ser | Glu | Ala | Val | Glu | Met | Met | Asp | Gln | Ile | Val | His | Trp | Val | Arg | Glu |
| 145 |     |     |     |     | 150 |     |     |     |     | 155 |     |     |     |     | 160 |
| Asp | Pro | Ser | Gly | Leu | Gly | Arg | Pro | Gln | Leu | Pro | Gly | Ala | Val | Ala | Ser |
|     |     |     | 165 |     |     |     |     | 170 |     |     |     |     | 175 |     |     |
| Glu | Ser | Met | Ala | Val | Pro | Met | Met | Leu | Leu | Cys | Leu | Val | Glu | Gln | Leu |
|     |     |     | 180 |     |     |     | 185 |     |     |     |     |     | 190 |     |     |
| Gly | Glu | Glu | Asp | Glu | Glu | Leu | Ala | Gly | Arg | Tyr | Ala | Gln | Leu | Gly | His |
|     |     | 195 |     |     |     |     | 200 |     |     |     |     | 205 |     |     |     |
| Trp | Cys | Ala | Arg | Arg | Ile | Leu | Gln | His | Val | Gln | Arg | Asp | Gly | Gln | Ala |
|     | 210 |     |     |     |     | 215 |     |     |     |     | 220 |     |     |     |     |
| Val | Leu | Glu | Asn | Val | Ser | Glu | Asp | Gly | Glu | Glu | Leu | Ser | Gly | Cys | Leu |
| 225 |     |     |     |     | 230 |     |     |     |     | 235 |     |     |     |     | 240 |
| Gly | Arg | His | Gln | Asn | Pro | Gly | His | Ala | Leu | Glu | Ala | Gly | Trp | Phe | Leu |
|     |     |     |     | 245 |     |     |     |     | 250 |     |     |     |     | 255 |     |
| Leu | Arg | His | Ser | Ser | Arg | Ser | Gly | Asp | Ala | Lys | Leu | Arg | Ala | His | Val |
|     |     |     | 260 |     |     |     |     | 265 |     |     |     | 270 |     |     |     |
| Ile | Asp | Thr | Phe | Leu | Leu | Leu | Pro | Phe | Arg | Ser | Gly | Trp | Asp | Ala | Asp |
|     |     | 275 |     |     |     |     | 280 |     |     |     |     | 285 |     |     |     |
| Tyr | Gly | Gly | Leu | Phe | Tyr | Phe | Gln | Asp | Ala | Asp | Gly | Leu | Cys | Pro | Thr |
|     | 290 |     |     |     |     | 295 |     |     |     | 300 |     |     |     |     |     |
| Gln | Leu | Glu | Trp | Ala | Met | Lys | Leu | Trp | Trp | Pro | His | Arg | Gln | Ala | Met |
| 305 |     |     |     |     | 310 |     |     |     |     | 315 |     |     |     |     | 320 |
| Ile | Ala | Phe | Leu | Met | Gly | Tyr | Ser | Glu | Ser | Gly | Asp | Pro | Ala | Leu | Leu |
|     |     |     |     | 325 |     |     |     |     | 330 |     |     |     |     | 335 |     |
| Arg | Leu | Phe | Tyr | Gln | Val | Ala | Glu | Tyr | Thr | Phe | Arg | Gln | Phe | Arg | Asp |
|     |     |     | 340 |     |     |     |     | 345 |     |     |     | 350 |     |     |     |
| Pro | Glu | Tyr | Gly | Glu | Trp | Phe | Gly | Tyr | Leu | Asn | Arg | Glu | Gly | Lys | Val |
|     |     | 355 |     |     |     |     | 360 |     |     |     | 365 |     |     |     |     |
| Ala | Leu | Thr | Ile | Lys | Gly | Gly | Pro | Phe | Lys | Gly | Cys | Phe | His | Val | Pro |
|     | 370 |     |     |     | 375 |     |     |     |     | 380 |     |     |     |     |     |
| Arg | Cys | Leu | Ala | Met | Cys | Glu | Glu | Met | Leu | Ser | Ala | Leu | Leu | Ser | Arg |
| 385 |     |     |     | 390 |     |     |     |     | 395 |     |     |     |     |     | 400 |
| Leu | Ala |     |     |     |     |     |     |     |     |     |     |     |     |     |     |

( 2 ) INFORMATION FOR SEQ ID NO:5:

( i ) SEQUENCE CHARACTERISTICS:
        ( A ) LENGTH: 1209 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

| ATGGAGAAGG | AGCGCGAAAC | TCTGCAGGCC | TGGAAGGAGC | GTGTGGGCCA | AGAGCTGGAC | 60  |
|------------|------------|------------|------------|------------|------------|-----|
| CGCGTGATGG | CTTTCTGGCT | GGAGCACTCC | CACGATCGGG | AGCACGGGGG | CTTCTTCACG | 120 |
| TGCCTGGGCC | GCGACGGGCG | GGTGTATGAC | GACCTCAAGT | ACGTCTGGCT | GCAGGGGAGG | 180 |

-continued

```
CAGGTGTGGA  TGTACTGTCG  CCTGTACCGC  AAGCTTGAGC  GCTTCCACCG  CCCTGAGCTT    240
CTGGATGCGG  CTAAAGCAGG  GGGCGAATTT  TTGCTGCGCC  ATGCCCGAGT  GGCACCTCCT    300
GAAAAGAAGT  GTGCCTTTGT  GCTGACGCGG  GACGGCCGGC  CCGTCAAGGT  GCAGCGGAGC    360
ATCTTCAGTG  AGTGCTTCTA  CACCATGGCC  ATGAACGAGC  TGTGGAGGGT  GACGGCGGAG    420
GCACGGTACC  AGAGCGAAGC  GGTGGACATG  ATGGATCAGA  TCGTGCACTG  GGTGCGAGAG    480
GACCCCTCTG  GGCTGGGCCG  GCCCCAGCTC  CCCGGGGCCG  TGGCCTCGGA  GTCCATGGCA    540
GTGCCCATGA  TGCTGCTGTG  CCTGGTGGAG  CAGCTCGGGG  AGGAGGACGA  GGAGCTGGCA    600
GGCCGCTACG  CGCAGCTGGG  GCACTGGTGC  GCTCGGAGGA  TCCTGCAGCA  CGTCCAGAGG    660
GATGGACAGG  CTGTGCTGGA  GAATGTGTCG  GAAGATGGCG  AGGAACTTTC  TGGCTGCCTG    720
GGGAGACACC  AGAACCCAGG  CCACGCGCTG  GAAGCTGGCT  GGTTCCTGCT  CCGCCACAGC    780
AGCCGGAGCG  GTGACGCCAA  ACTTCGAGCC  CACGTCATCG  ACACGTTCCT  GCTACTGCCT    840
TTCCGCTCCG  GATGGGACGC  TGATCACGGA  GGCCTCTTCT  ACTTCCAGGA  TGCCGATGGC    900
CTCTGCCCCA  CCCAGCTGGA  GTGGGCCATG  AAGCTCTGGT  GGCCGCACAG  CGAAGCCATG    960
ATCGCCTTTC  TCATGGGCTA  CAGTGAGAGC  GGGGACCCTG  CCTTACTGCG  TCTCTTCTAC   1020
CAGGTGGCCG  AGTACACGTT  TCGCCAGTTT  CGTGATCCCG  AGTACGGGGA  ATGGTTTGGC   1080
TACCTGAACC  GAGAGGGGAA  GGTTGCCCTC  ACTATCAAGG  GGGTCCCTT   TAAAGGCTGC   1140
TTCCACGTGC  CGCGGTGCCT  TGCCATGTGC  GAAGAGATGC  TGAGCGCCCT  GCTGAGCCGC   1200
CTCGCCTAG                                                                1209
```

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:6:

```
Pro  Ala  Pro  Ser  Pro  Ala  Pro  Thr  Pro  Ala  Cys  Arg  Gly  Ala  Glu
 1              5                        10                           15
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:7:

```
Pro  Ala  Pro  Leu  Gly  Ser  Leu  Pro  Ala  Val  Pro  Thr  Arg  Glu  Gly  Ser
 1              5                        10                           15
Lys
```

( 2 ) INFORMATION FOR SEQ ID NO:8:

( i ) SEQUENCE CHARACTERISTICS:
        ( A ) LENGTH: 8 amino acids
        ( B ) TYPE: amino acid (C) STRANDEDNESS: single
(D) TOPOLOGY: linear (ii) MOLECULE TYPE: peptide (v) FRAGMENT TYPE: internal (xi) SEQUENCE DESCRIPTION: SEQ ID NO:8:

```
Lys Gly Asn Lys Ser Trp Gln Asp
 1               5
```

(2) INFORMATION FOR SEQ ID NO:9:

(i) SEQUENCE CHARACTERISTICS:
   (A) LENGTH: 1209 base pairs
   (B) TYPE: nucleic acid
   (C) STRANDEDNESS: single
   (D) TOPOLOGY: linear (ii) MOLECULE TYPE: cDNA (ix) FEATURE:
   (A) NAME/KEY: Coding Sequence
   (B) LOCATION: 1...1206
   (D) OTHER INFORMATION:

(xi) SEQUENCE DESCRIPTION: SEQ ID NO:9:

```
ATG GAG AAG GAG CGC GAA ACT CTG CAG GCC TGG AAG GAG CGT GTG GGC    48
Met Glu Lys Glu Arg Glu Thr Leu Gln Ala Trp Lys Glu Arg Val Gly
 1               5                  10                  15

CAA GAG CTG GAC CGC GTG ATG GCT TTC TGG CTG GAG CAC TCC CAC GAT    96
Gln Glu Leu Asp Arg Val Met Ala Phe Trp Leu Glu His Ser His Asp
                20                  25                  30

CGG GAG CAC GGG GGC TTC TTC ACG TGC CTG GGC CGC GAC GGG CGG GTG    144
Arg Glu His Gly Gly Phe Phe Thr Cys Leu Gly Arg Asp Gly Arg Val
             35                  40                  45

TAT GAC GAC CTC AAG TAC GTC TGG CTG CAG GGG AGG CAG GTG TGG ATG    192
Tyr Asp Asp Leu Lys Tyr Val Trp Leu Gln Gly Arg Gln Val Trp Met
         50                  55                  60

TAC TGT CGC CTG TAC CGC AAG CTT GAG CGC TTC CAC CGC CCT GAG CTT    240
Tyr Cys Arg Leu Tyr Arg Lys Leu Glu Arg Phe His Arg Pro Glu Leu
 65                  70                  75                  80

CTG GAT GCG GCT AAA GCA GGG GGC GAA TTT TTG CTG CGC CAT GCC CGA    288
Leu Asp Ala Ala Lys Ala Gly Gly Glu Phe Leu Leu Arg His Ala Arg
                 85                  90                  95

GTG GCA CCT CCT GAA AAG AAG TGT GCC TTT GTG CTG ACG CGG GAC GGC    336
Val Ala Pro Pro Glu Lys Lys Cys Ala Phe Val Leu Thr Arg Asp Gly
                100                 105                 110

CGG CCC GTC AAG GTG CAG CGG AGC ATC TTC AGT GAG TGC TTC TAC ACC    384
Arg Pro Val Lys Val Gln Arg Ser Ile Phe Ser Glu Cys Phe Tyr Thr
            115                 120                 125

ATG GCC ATG AAC GAG CTG TGG AGG GTG ACG GCG GAG GCA CGG TAC CAG    432
Met Ala Met Asn Glu Leu Trp Arg Val Thr Ala Glu Ala Arg Tyr Gln
        130                 135                 140

AGC GAA GCG GTG GAC ATG ATG GAT CAG ATC GTG CAC TGG GTG CGA GAG    480
Ser Glu Ala Val Asp Met Met Asp Gln Ile Val His Trp Val Arg Glu
145                 150                 155                 160

GAC CCC TCT GGG CTG GGC CGG CCC CAG CTC CCC GGG GCC GTG GCC TCG    528
Asp Pro Ser Gly Leu Gly Arg Pro Gln Leu Pro Gly Ala Val Ala Ser
                165                 170                 175

GAG TCC ATG GCA GTG CCC ATG ATG CTG CTG TGC CTG GTG GAG CAG CTC    576
Glu Ser Met Ala Val Pro Met Met Leu Leu Cys Leu Val Glu Gln Leu
                180                 185                 190

GGG GAG GAG GAC GAG GAG CTG GCA GGC CGC TAC GCG CAG CTG GGG CAC    624
Gly Glu Glu Asp Glu Glu Leu Ala Gly Arg Tyr Ala Gln Leu Gly His
```

|  |  |  | 195 |  |  |  |  | 200 |  |  |  |  | 205 |  |  |  |
|---|---|---|---|---|---|---|---|---|---|---|---|---|---|---|---|---|
| TGG | TGC | GCT | CGG | AGG | ATC | CTG | CAG | CAC | GTC | CAG | AGG | GAT | GGA | CAG | GCT | 672 |
| Trp | Cys 210 | Ala | Arg | Arg | Ile | Leu 215 | Gln | His | Val | Gln | Arg 220 | Asp | Gly | Gln | Ala |  |
| GTG | CTG | GAG | AAT | GTG | TCG | GAA | GAT | GGC | GAG | GAA | CTT | TCT | GGC | TGC | CTG | 720 |
| Val 225 | Leu | Glu | Asn | Val | Ser 230 | Glu | Asp | Gly | Glu | Glu 235 | Leu | Ser | Gly | Cys | Leu 240 |  |
| GGG | AGA | CAC | CAG | AAC | CCA | GGC | CAC | GCG | CTG | GAA | GCT | GGC | TGG | TTC | CTG | 768 |
| Gly | Arg | His | Gln | Asn 245 | Pro | Gly | His | Ala | Leu 250 | Glu | Ala | Gly | Trp | Phe 255 | Leu |  |
| CTC | CGC | CAC | AGC | AGC | CGG | AGC | GGT | GAC | GCC | AAA | CTT | CGA | GCC | CAC | GTC | 816 |
| Leu | Arg | His | Ser 260 | Ser | Arg | Ser | Gly | Asp 265 | Ala | Lys | Leu | Arg | Ala 270 | His | Val |  |
| ATC | GAC | ACG | TTC | CTG | CTA | CTG | CCT | TTC | CGC | TCC | GGA | TGG | GAC | GCT | GAT | 864 |
| Ile | Asp | Thr 275 | Phe | Leu | Leu | Leu | Pro 280 | Phe | Arg | Ser | Gly | Trp 285 | Asp | Ala | Asp |  |
| CAC | GGA | GGC | CTC | TTC | TAC | TTC | CAG | GAT | GCC | GAT | GGC | CTC | TGC | CCC | ACC | 912 |
| His | Gly 290 | Gly | Leu | Phe | Tyr | Phe 295 | Gln | Asp | Ala | Asp | Gly 300 | Leu | Cys | Pro | Thr |  |
| CAG | CTG | GAG | TGG | GCC | ATG | AAG | CTC | TGG | TGG | CCG | CAC | AGC | GAA | GCC | ATG | 960 |
| Gln 305 | Leu | Glu | Trp | Ala | Met 310 | Lys | Leu | Trp | Trp | Pro 315 | His | Ser | Glu | Ala | Met 320 |  |
| ATC | GCC | TTT | CTC | ATG | GGC | TAC | AGT | GAG | AGC | GGG | GAC | CCT | GCC | TTA | CTG | 1008 |
| Ile | Ala | Phe | Leu | Met 325 | Gly | Tyr | Ser | Glu | Ser 330 | Gly | Asp | Pro | Ala | Leu 335 | Leu |  |
| CGT | CTC | TTC | TAC | CAG | GTG | GCC | GAG | TAC | ACG | TTT | CGC | CAG | TTT | CGT | GAT | 1056 |
| Arg | Leu | Phe | Tyr 340 | Gln | Val | Ala | Glu | Tyr 345 | Thr | Phe | Arg | Gln | Phe 350 | Arg | Asp |  |
| CCC | GAG | TAC | GGG | GAA | TGG | TTT | GGC | TAC | CTG | AAC | CGA | GAG | GGG | AAG | GTT | 1104 |
| Pro | Glu | Tyr 355 | Gly | Glu | Trp | Phe | Gly 360 | Tyr | Leu | Asn | Arg | Glu 365 | Gly | Lys | Val |  |
| GCC | CTC | ACT | ATC | AAG | GGG | GGT | CCC | TTT | AAA | GGC | TGC | TTC | CAC | GTG | CCG | 1152 |
| Ala | Leu 370 | Thr | Ile | Lys | Gly | Gly 375 | Pro | Phe | Lys | Gly | Cys 380 | Phe | His | Val | Pro |  |
| CGG | TGC | CTT | GCC | ATG | TGC | GAA | GAG | ATG | CTG | AGC | GCC | CTG | CTG | AGC | CGC | 1200 |
| Arg 385 | Cys | Leu | Ala | Met | Cys 390 | Glu | Glu | Met | Leu | Ser 395 | Ala | Leu | Leu | Ser | Arg 400 |  |
| CTC | GCC | TAG |  |  |  |  |  |  |  |  |  |  |  |  |  | 1209 |
| Leu | Ala |  |  |  |  |  |  |  |  |  |  |  |  |  |  |  |